US008696596B2

(12) United States Patent
Douglas et al.

(10) Patent No.: US 8,696,596 B2
(45) Date of Patent: *Apr. 15, 2014

(54) BLOOD AND INTERSTITIAL FLUID SAMPLING DEVICE

(75) Inventors: Joel S. Douglas, Groton, CT (US);
Jeffrey N. Roe, San Ramon, CA (US);
Ryszard Radwanski, Lublin (PL);
Henry M. Grage, Alpharetta, GA (US);
Michael S. Sanchez, Mountain View, CA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 300 days.

This patent is subject to a terminal disclaimer.

(21) Appl. No.: 12/644,528

(22) Filed: Dec. 22, 2009

(65) Prior Publication Data
US 2010/0106058 A1    Apr. 29, 2010

Related U.S. Application Data

(60) Division of application No. 10/835,094, filed on Apr. 29, 2004, now Pat. No. 7,666,150, which is a continuation of application No. 09/988,799, filed on Nov. 20, 2001, now Pat. No. 6,793,633, which is a continuation of application No. 09/180,839, filed as application No. PCT/US97/08762 on May 16, 1997, now Pat. No. 6,332,871.

(60) Provisional application No. 60/017,133, filed on May 17, 1996.

(51) Int. Cl.
*A61B 5/00*    (2006.01)
*A61B 17/14*   (2006.01)
*A61B 17/32*   (2006.01)

(52) U.S. Cl.
USPC .......................................... 600/583; 606/181

(58) Field of Classification Search
USPC ................... 600/583, 584, 573; 606/181–183
See application file for complete search history.

(56) References Cited

U.S. PATENT DOCUMENTS

| 1,275,414 A | 8/1918 | Forbes |
| 1,960,889 A | 5/1934 | Benedict |

(Continued)

FOREIGN PATENT DOCUMENTS

| DE | 1 938 870 | 1/1970 |
| DE | 37 08 031 A1 | 11/1987 |

(Continued)

OTHER PUBLICATIONS

Brace et al., "Re-evaluation of the Needle Method for Measuring Interstitial Fluid Pressure", American Journal of Physiology, 1975, vol./Issue No. 229 (3), pp. 603-607, American Physiological Society.

(Continued)

*Primary Examiner* — Brian Szmal
(74) *Attorney, Agent, or Firm* — Woodard, Emhardt, Moriarty, McNett & Henry LLP

(57) ABSTRACT

A device and method for lancing a patient, virtually simultaneously producing and collecting a small fluid sample from a body. The device comprises a blood collection system including a lancing needle (16), drive mechanism (11), kneading or vibration mechanism (25), optional suction system (7), and sample ejection mechanism. The device is preferably sized to be hand-held in one hand and operable with one hand. The device can optionally contain integral testing or analysis component (83) for receiving the sample and providing testing or analysis indication or readout for the user. A method involves piercing the skin at a rapid rate, kneading the surrounding area by ultrasonic action, piezoelectric or mechanical oscillation to stimulate the blood flow from the wound, drawing the fluid using a pumping system.

14 Claims, 23 Drawing Sheets

(56) References Cited

U.S. PATENT DOCUMENTS

| | | |
|---|---|---|
| 2,594,621 A | 4/1952 | Derrick |
| 2,646,799 A | 7/1953 | Jacoby |
| 2,714,890 A | 8/1955 | Vang |
| 3,030,959 A | 4/1962 | Grunert |
| 3,040,744 A | 6/1962 | Hoggard |
| 3,068,868 A | 12/1962 | Skopyk |
| 3,086,288 A | 4/1963 | Balamuth et al. |
| 3,208,452 A | 9/1965 | Stern |
| 3,221,739 A | 12/1965 | Rosenthal |
| 3,235,337 A | 2/1966 | Artis |
| 3,358,689 A | 12/1967 | Higgins |
| 3,486,504 A | 12/1969 | Austin |
| 3,626,929 A | 12/1971 | Sanz et al. |
| 3,673,475 A | 6/1972 | Britton, Jr. |
| 3,734,085 A | 5/1973 | Russell |
| 3,741,197 A | 6/1973 | Sanz et al. |
| 3,774,611 A | 11/1973 | Tussey et al. |
| 3,832,776 A | 9/1974 | Sawyer |
| 3,933,439 A | 1/1976 | McDonald |
| D238,710 S | 2/1976 | Cacanindin |
| 3,964,482 A | 6/1976 | Gerstel et al. |
| 4,077,406 A | 3/1978 | Sandhage et al. |
| 4,151,832 A | 5/1979 | Hamer |
| 4,154,228 A | 5/1979 | Feldstein et al. |
| D254,444 S | 3/1980 | Levine |
| 4,203,446 A | 5/1980 | Hofert et al. |
| 4,222,380 A | 9/1980 | Terayama |
| 4,223,674 A | 9/1980 | Fluent et al. |
| 4,230,118 A | 10/1980 | Holman et al. |
| 4,235,234 A | 11/1980 | Whitney et al. |
| 4,356,826 A | 11/1982 | Kubota |
| 4,360,016 A | 11/1982 | Sarrine |
| 4,368,738 A | 1/1983 | Tersteegen et al. |
| 4,375,815 A | 3/1983 | Burns |
| 4,383,530 A | 5/1983 | Bruno |
| 4,397,643 A | 8/1983 | Rygiel |
| 4,441,510 A | 4/1984 | Worley et al. |
| 4,449,529 A | 5/1984 | Burns et al. |
| 4,460,354 A | 7/1984 | Weilbacher et al. |
| 4,462,405 A | 7/1984 | Erhlich |
| 4,469,110 A | 9/1984 | Slama |
| 4,503,856 A | 3/1985 | Cornell et al. |
| 4,517,978 A | 5/1985 | Levin et al. |
| 4,518,384 A | 5/1985 | Tarello et al. |
| 4,535,773 A | 8/1985 | Yoon |
| 4,553,541 A | 11/1985 | Burns |
| 4,564,513 A | 1/1986 | Becher et al. |
| 4,577,630 A | 3/1986 | Nitzsche et al. |
| 4,580,564 A | 4/1986 | Anderson |
| 4,622,974 A | 11/1986 | Coleman et al. |
| 4,627,445 A | 12/1986 | Garcia et al. |
| 4,637,403 A | 1/1987 | Garcia et al. |
| 4,637,978 A | 1/1987 | Dappen |
| 4,648,408 A | 3/1987 | Hutcheson et al. |
| 4,653,511 A | 3/1987 | Goch |
| 4,653,513 A | 3/1987 | Dombrowski |
| 4,658,821 A | 4/1987 | Chiodo et al. |
| 4,660,570 A | 4/1987 | Dombrowski |
| 4,677,979 A | 7/1987 | Burns |
| 4,685,463 A | 8/1987 | Williams |
| 4,687,000 A | 8/1987 | Eisenhardt et al. |
| 4,750,489 A | 6/1988 | Berkman et al. |
| 4,772,264 A | 9/1988 | Cragg |
| 4,787,398 A | 11/1988 | Garcia et al. |
| 4,790,979 A | 12/1988 | Terminiello et al. |
| 4,794,926 A | 1/1989 | Munsch et al. |
| 4,805,623 A | 2/1989 | Jobsis |
| 4,823,806 A | 4/1989 | Bajada |
| RE32,922 E | 5/1989 | Levin et al. |
| 4,844,095 A | 7/1989 | Chiodo et al. |
| 4,850,973 A | 7/1989 | Jordan et al. |
| 4,858,607 A | 8/1989 | Jordan et al. |
| 4,869,249 A | 9/1989 | Crossman et al. |
| 4,873,993 A | 10/1989 | Meserol et al. |
| 4,883,068 A | 11/1989 | Dechow |
| D305,065 S | 12/1989 | Büchel et al. |
| 4,895,147 A | 1/1990 | Bodicky et al. |
| 4,920,977 A | 5/1990 | Haynes |
| 4,924,879 A | 5/1990 | O'Brien |
| 4,925,447 A | 5/1990 | Rosenblatt |
| 4,953,552 A | 9/1990 | DeMarzo |
| 4,976,724 A | 12/1990 | Nieto et al. |
| 4,981,473 A | 1/1991 | Rosenblatt |
| 4,983,178 A | 1/1991 | Schnell |
| 4,990,154 A | 2/1991 | Brown et al. |
| 4,994,068 A | 2/1991 | Hufnagle |
| 4,994,073 A | 2/1991 | Green |
| 4,995,402 A | 2/1991 | Smith et al. |
| 5,002,054 A | 3/1991 | Ash et al. |
| 5,014,718 A | 5/1991 | Mitchen |
| 5,019,059 A | 5/1991 | Goldberg et al. |
| 5,029,583 A | 7/1991 | Meserol et al. |
| 5,035,704 A | 7/1991 | Lambert et al. |
| 5,047,044 A | 9/1991 | Smith et al. |
| 5,052,403 A | 10/1991 | Haber et al. |
| 5,054,499 A | 10/1991 | Swierczek |
| 5,066,859 A | 11/1991 | Karkar et al. |
| 5,070,884 A | 12/1991 | Columbus et al. |
| 5,070,886 A | 12/1991 | Mitchen et al. |
| D324,423 S | 3/1992 | Ahlstrand et al. |
| 5,097,810 A | 3/1992 | Fishman et al. |
| 5,102,404 A | 4/1992 | Goldberg et al. |
| 5,108,889 A | 4/1992 | Smith |
| 5,145,565 A | 9/1992 | Kater et al. |
| 5,152,775 A | 10/1992 | Ruppert |
| 5,163,442 A | 11/1992 | Ono |
| 5,165,418 A | 11/1992 | Tankovich |
| D332,306 S | 1/1993 | Garth et al. |
| 5,188,118 A | 2/1993 | Terwilliger |
| 5,189,751 A | 3/1993 | Giuliani et al. |
| 5,193,552 A | 3/1993 | Columbus et al. |
| 5,195,534 A | 3/1993 | Sarrine |
| 5,201,324 A | 4/1993 | Swierczek |
| 5,217,480 A | 6/1993 | Haber et al. |
| 5,222,504 A | 6/1993 | Solomon |
| 5,231,993 A | 8/1993 | Haber et al. |
| 5,269,800 A | 12/1993 | Davis, Jr. |
| 5,271,385 A | 12/1993 | Bailey |
| 5,277,198 A | 1/1994 | Kanner et al. |
| 5,279,294 A | 1/1994 | Anderson et al. |
| 5,279,586 A | 1/1994 | Balkwill |
| 5,282,822 A | 2/1994 | Macors et al. |
| 5,304,193 A | 4/1994 | Zhadanov |
| 5,309,924 A | 5/1994 | Peabody |
| 5,314,441 A | 5/1994 | Cusack et al. |
| 5,314,442 A | 5/1994 | Morita |
| 5,318,583 A | 6/1994 | Rabenau et al. |
| 5,318,584 A | 6/1994 | Lange et al. |
| 5,320,607 A | 6/1994 | Ishibashi |
| 5,320,808 A | 6/1994 | Holen et al. |
| 5,324,302 A | 6/1994 | Crouse |
| 5,324,303 A | 6/1994 | Strong et al. |
| 5,353,806 A | 10/1994 | Heinzelman et al. |
| 5,366,470 A | 11/1994 | Ramel |
| 5,368,047 A | 11/1994 | Suzuki et al. |
| 5,387,203 A | 2/1995 | Goodrich |
| 5,395,387 A | 3/1995 | Burns |
| 5,402,798 A | 4/1995 | Swierczek et al. |
| 5,415,169 A | 5/1995 | Siczek et al. |
| 5,421,816 A | 6/1995 | Lipkovker |
| 5,423,758 A | 6/1995 | Shaw |
| 5,423,847 A | 6/1995 | Strong et al. |
| 5,437,640 A | 8/1995 | Schwab |
| 5,445,611 A | 8/1995 | Eppstein et al. |
| 5,456,875 A | 10/1995 | Lambert |
| 5,458,140 A | 10/1995 | Eppstein et al. |
| 5,472,427 A | 12/1995 | Rammler |
| 5,474,084 A | 12/1995 | Cunniff |
| 5,487,748 A | 1/1996 | Marshall et al. |
| 5,510,266 A | 4/1996 | Bonner et al. |
| 5,512,158 A | 4/1996 | Cole |
| 5,514,152 A | 5/1996 | Smith |
| 5,518,006 A | 5/1996 | Mawhirt et al. |
| 5,529,074 A | 6/1996 | Greenfield |

(56) References Cited

U.S. PATENT DOCUMENTS

| | | |
|---|---|---|
| D371,440 S | 7/1996 | Petersen |
| 5,540,709 A | 7/1996 | Ramel |
| 5,545,173 A | 8/1996 | Herbst |
| 5,545,174 A | 8/1996 | Schenk et al. |
| 5,549,584 A | 8/1996 | Gross |
| 5,554,166 A | 9/1996 | Lange et al. |
| 5,569,212 A | 10/1996 | Brown |
| 5,575,403 A | 11/1996 | Charlton et al. |
| 5,582,184 A | 12/1996 | Erickson et al. |
| D378,612 S | 3/1997 | Clark et al. |
| 5,607,401 A | 3/1997 | Humphrey |
| 5,611,809 A | 3/1997 | Marshall et al. |
| 5,613,978 A | 3/1997 | Harding |
| 5,624,458 A | 4/1997 | Lipscher |
| 5,628,309 A | 5/1997 | Brown |
| 5,628,764 A | 5/1997 | Schraga |
| 5,628,765 A | 5/1997 | Morita |
| 5,630,986 A | 5/1997 | Charlton et al. |
| 5,632,410 A | 5/1997 | Moulton et al. |
| 5,638,828 A | 6/1997 | Lauks et al. |
| 5,662,127 A | 9/1997 | De Vaughn |
| 5,671,753 A | 9/1997 | Pitesky |
| 5,680,872 A | 10/1997 | Sesekura et al. |
| 5,682,233 A | 10/1997 | Brinda |
| 5,700,695 A | 12/1997 | Yassinzadeh et al. |
| 5,707,384 A | 1/1998 | Kim |
| 5,709,699 A | 1/1998 | Warner |
| 5,714,390 A | 2/1998 | Hallowitz et al. |
| 5,720,924 A | 2/1998 | Eikmeier et al. |
| 5,730,357 A | 3/1998 | Besenchek et al. |
| 5,730,753 A | 3/1998 | Morita |
| 5,738,244 A | 4/1998 | Charlton et al. |
| 5,741,291 A | 4/1998 | Yoo |
| RE35,803 E | 5/1998 | Lange et al. |
| 5,746,217 A | 5/1998 | Erickson et al. |
| 5,755,733 A | 5/1998 | Morita |
| 5,758,643 A | 6/1998 | Wong et al. |
| 5,776,157 A | 7/1998 | Thorne et al. |
| 5,788,651 A | 8/1998 | Weilandt |
| 5,788,652 A | 8/1998 | Rahn |
| 5,800,781 A | 9/1998 | Gavin et al. |
| 5,801,057 A | 9/1998 | Smart et al. |
| 5,810,199 A | 9/1998 | Charlton et al. |
| 5,823,973 A | 10/1998 | Racchini et al. |
| 5,830,219 A | 11/1998 | Bird et al. |
| 5,846,490 A | 12/1998 | Yokota et al. |
| 5,851,215 A | 12/1998 | Mawhirt et al. |
| 5,854,074 A | 12/1998 | Charlton et al. |
| 5,855,801 A | 1/1999 | Lin et al. |
| 5,857,983 A | 1/1999 | Douglas et al. |
| 5,863,800 A | 1/1999 | Eikmeier et al. |
| 5,871,494 A | 2/1999 | Simons et al. |
| 5,873,887 A | 2/1999 | King et al. |
| 5,879,311 A | 3/1999 | Duchon et al. |
| 5,880,829 A | 3/1999 | Kauhaniemi et al. |
| 5,885,211 A | 3/1999 | Eppstein et al. |
| 5,885,219 A | 3/1999 | Nightengale |
| 5,891,053 A | 4/1999 | Sesekura |
| 5,902,279 A | 5/1999 | Powles et al. |
| 5,913,833 A | 6/1999 | Elstrom et al. |
| 5,916,222 A | 6/1999 | Iwasaki et al. |
| 5,916,229 A | 6/1999 | Evans |
| 5,916,230 A | 6/1999 | Brenneman et al. |
| 5,935,075 A | 8/1999 | Casscells et al. |
| 5,938,679 A | 8/1999 | Freeman et al. |
| 5,951,492 A | 9/1999 | Douglas et al. |
| 5,951,582 A | 9/1999 | Thorne et al. |
| 5,964,718 A | 10/1999 | Duchon et al. |
| 5,968,063 A | 10/1999 | Chu et al. |
| 5,971,941 A | 10/1999 | Simons et al. |
| 5,984,940 A | 11/1999 | Davis et al. |
| 5,997,561 A | 12/1999 | Bocker et al. |
| 6,015,392 A | 1/2000 | Douglas et al. |
| 6,022,324 A | 2/2000 | Skinner |
| 6,022,366 A | 2/2000 | Schraga |
| 6,027,459 A | 2/2000 | Shain et al. |
| 6,036,924 A | 3/2000 | Simons et al. |
| 6,045,567 A | 4/2000 | Taylor et al. |
| 6,048,352 A | 4/2000 | Douglas et al. |
| 6,056,765 A | 5/2000 | Bajaj et al. |
| 6,063,039 A | 5/2000 | Cunningham et al. |
| 6,066,103 A | 5/2000 | Duchon et al. |
| 6,068,599 A | 5/2000 | Saito et al. |
| 6,071,249 A | 6/2000 | Cunningham et al. |
| 6,071,250 A | 6/2000 | Douglas et al. |
| 6,071,251 A | 6/2000 | Cunningham et al. |
| 6,071,294 A | 6/2000 | Simons et al. |
| 6,080,116 A | 6/2000 | Erickson et al. |
| 6,086,545 A | 7/2000 | Roe et al. |
| 6,090,078 A | 7/2000 | Erskine |
| 6,093,156 A | 7/2000 | Cunningham et al. |
| 6,117,630 A | 9/2000 | Reber et al. |
| 6,120,462 A | 9/2000 | Hibner et al. |
| 6,132,449 A | 10/2000 | Lum et al. |
| 6,136,013 A | 10/2000 | Marshall et al. |
| 6,139,562 A | 10/2000 | Mauze et al. |
| 6,143,164 A | 11/2000 | Heller et al. |
| 6,146,361 A | 11/2000 | DiBiasi et al. |
| 6,152,889 A | 11/2000 | Sopp et al. |
| 6,152,942 A | 11/2000 | Brenneman et al. |
| 6,155,992 A | 12/2000 | Henning et al. |
| 6,156,050 A | 12/2000 | Davis et al. |
| 6,156,051 A | 12/2000 | Schraga |
| 6,159,424 A | 12/2000 | Kauhaniemi et al. |
| 6,171,325 B1 | 1/2001 | Mauze et al. |
| 6,176,865 B1 | 1/2001 | Mauze et al. |
| 6,183,434 B1 | 2/2001 | Eppstein |
| 6,183,489 B1 | 2/2001 | Douglas et al. |
| 6,193,673 B1 | 2/2001 | Viola et al. |
| 6,203,504 B1 | 3/2001 | Latterell et al. |
| 6,206,841 B1 | 3/2001 | Cunningham et al. |
| 6,210,420 B1 | 4/2001 | Mauze et al. |
| 6,210,421 B1 | 4/2001 | Bocker et al. |
| 6,228,100 B1 | 5/2001 | Schraga |
| 6,231,531 B1 | 5/2001 | Lum et al. |
| 6,261,241 B1 | 7/2001 | Burbank et al. |
| 6,261,244 B1 | 7/2001 | Kensey et al. |
| 6,261,245 B1 | 7/2001 | Kawai et al. |
| 6,283,926 B1 | 9/2001 | Cunningham et al. |
| 6,283,982 B1 | 9/2001 | Levaughn et al. |
| 6,285,454 B1 | 9/2001 | Douglas et al. |
| 6,306,104 B1 | 10/2001 | Cunningham et al. |
| 6,306,152 B1 | 10/2001 | Verdonk et al. |
| 6,315,738 B1 | 11/2001 | Nishikawa et al. |
| 6,319,210 B1 | 11/2001 | Douglas et al. |
| 6,332,871 B1 | 12/2001 | Douglas et al. |
| 6,346,114 B1 | 2/2002 | Schraga |
| 6,352,514 B1 | 3/2002 | Douglas et al. |
| 6,364,889 B1 | 4/2002 | Kheiri et al. |
| 6,364,890 B1 | 4/2002 | Lum et al. |
| 6,375,627 B1 | 4/2002 | Mauze et al. |
| 6,379,317 B1 | 4/2002 | Kintzig et al. |
| 6,379,969 B1 | 4/2002 | Mauze et al. |
| 6,391,005 B1 | 5/2002 | Lum et al. |
| 6,402,701 B1 | 6/2002 | Kaplan et al. |
| 6,402,704 B1 | 6/2002 | McMorrow |
| 6,409,740 B1 | 6/2002 | Kuhr et al. |
| 6,419,661 B1 | 7/2002 | Kuhr et al. |
| 6,423,011 B1 | 7/2002 | Arulkumaran et al. |
| 6,461,496 B1 | 10/2002 | Feldman et al. |
| 6,464,649 B1 | 10/2002 | Duchon et al. |
| 6,472,220 B1 | 10/2002 | Simons et al. |
| 6,485,439 B1 | 11/2002 | Roe et al. |
| 6,488,891 B2 | 12/2002 | Mason et al. |
| 6,491,709 B2 | 12/2002 | Sharma et al. |
| 6,497,845 B1 | 12/2002 | Sacherer |
| 6,503,210 B1 | 1/2003 | Hirao et al. |
| 6,506,575 B1 | 1/2003 | Knappe et al. |
| 6,530,892 B1 | 3/2003 | Kelly |
| 6,589,260 B1 | 7/2003 | Schmelzeisen-Redeker et al. |
| 6,706,000 B2 | 3/2004 | Perez et al. |
| 6,706,159 B2 | 3/2004 | Moerman et al. |
| 6,730,046 B1 | 5/2004 | Hamamoto et al. |
| 6,743,211 B1 | 6/2004 | Prausnitz et al. |

(56) References Cited

U.S. PATENT DOCUMENTS

| | | |
|---|---|---|
| 6,752,817 B2 | 6/2004 | Flora et al. |
| 6,793,633 B2 * | 9/2004 | Douglas et al. ............... 600/583 |
| 6,808,499 B1 | 10/2004 | Churchill et al. |
| 6,837,858 B2 | 1/2005 | Cunningham et al. |
| 7,041,068 B2 | 5/2006 | Freeman et al. |
| 7,247,144 B2 | 7/2007 | Douglas et al. |
| 7,731,668 B2 | 6/2010 | Douglas et al. |
| 2001/0011157 A1 | 8/2001 | Latterell et al. |
| 2001/0027327 A1 | 10/2001 | Schraga |
| 2001/0031931 A1 | 10/2001 | Cunningham et al. |
| 2001/0039387 A1 | 11/2001 | Rutynowski et al. |
| 2001/0044615 A1 | 11/2001 | Amano et al. |
| 2002/0002344 A1 | 1/2002 | Douglas et al. |
| 2002/0004196 A1 | 1/2002 | Whitson |
| 2002/0022789 A1 | 2/2002 | Perez et al. |
| 2002/0029059 A1 | 3/2002 | Purcell |
| 2002/0040230 A1 | 4/2002 | Kuhr et al. |
| 2002/0052618 A1 | 5/2002 | Haar et al. |
| 2002/0077584 A1 | 6/2002 | Lin et al. |
| 2002/0082522 A1 | 6/2002 | Douglas et al. |
| 2002/0082543 A1 | 6/2002 | Park et al. |
| 2002/0087110 A1 | 7/2002 | Effenhauser et al. |
| 2002/0103499 A1 | 8/2002 | Perez et al. |
| 2002/0115967 A1 | 8/2002 | Svedman |
| 2002/0169470 A1 | 11/2002 | Kuhr et al. |
| 2002/0177761 A1 | 11/2002 | Orloff et al. |
| 2002/0177788 A1 | 11/2002 | Hodges et al. |
| 2003/0083685 A1 | 5/2003 | Freeman et al. |
| 2003/0083686 A1 | 5/2003 | Freeman et al. |
| 2003/0088191 A1 | 5/2003 | Freeman et al. |
| 2003/0093093 A1 | 5/2003 | Modesitt et al. |
| 2003/0199789 A1 | 10/2003 | Boecker et al. |
| 2003/0199790 A1 | 10/2003 | Boecker et al. |
| 2003/0199791 A1 | 10/2003 | Boecker et al. |
| 2003/0199901 A1 | 10/2003 | Boecker et al. |
| 2003/0199903 A1 | 10/2003 | Boecker et al. |
| 2003/0199909 A1 | 10/2003 | Boecker et al. |
| 2003/0199911 A1 | 10/2003 | Boecker et al. |
| 2003/0212424 A1 | 11/2003 | Briggs et al. |
| 2003/0233112 A1 | 12/2003 | Alden et al. |
| 2003/0233113 A1 | 12/2003 | Alden et al. |
| 2006/0178690 A1 | 8/2006 | Freeman et al. |
| 2008/0015425 A1 | 1/2008 | Douglas et al. |
| 2012/0215084 A1 | 8/2012 | Douglas et al. |

FOREIGN PATENT DOCUMENTS

| | | |
|---|---|---|
| EP | 0 212 906 A2 | 3/1987 |
| EP | 0 453 283 A1 | 10/1991 |
| EP | 0 568 024 A2 | 11/1993 |
| EP | 0 622 046 A2 | 2/1994 |
| EP | 0 671 146 A1 | 9/1995 |
| EP | 0 688 532 A2 | 12/1995 |
| GB | 2 222 251 A | 2/1990 |
| JP | H02-170388 A | 7/1990 |
| JP | H04-194660 | 7/1992 |
| JP | H06-004150 A | 1/1994 |
| JP | H09-084781 | 3/1997 |
| JP | H09-084781 A | 3/1997 |
| JP | H09-276235 | 10/1997 |
| JP | H11-164825 A | 6/1999 |
| JP | 2000-116768 A2 | 4/2000 |
| JP | 2000-152923 A | 6/2000 |
| JP | 2001-095787 A | 4/2001 |
| WO | 85/04089 A1 | 9/1985 |
| WO | 93/02720 A1 | 2/1993 |
| WO | 93/09723 | 5/1993 |
| WO | 93/09723 A1 | 5/1993 |
| WO | 93/12726 A1 | 7/1993 |
| WO | 94/16737 A1 | 8/1994 |
| WO | 95/10223 A2 | 4/1995 |
| WO | 96/32635 A1 | 10/1996 |
| WO | 96/37256 A1 | 11/1996 |
| WO | 97/08986 A1 | 3/1997 |
| WO | 97/42882 A1 | 11/1997 |
| WO | 97/42885 A1 | 11/1997 |
| WO | 97/42886 A1 | 11/1997 |
| WO | 97/42888 A1 | 11/1997 |
| WO | 97/43962 A1 | 11/1997 |
| WO | WO 9742888 A1 | 11/1997 |
| WO | 99/26539 A1 | 6/1999 |
| WO | 99/55232 A1 | 11/1999 |
| WO | 00/45708 A1 | 8/2000 |
| WO | 01/00090 A1 | 1/2001 |
| WO | 01/34029 A1 | 5/2001 |
| WO | 01/64105 A1 | 9/2001 |
| WO | 01/66010 A1 | 9/2001 |
| WO | 01/72220 A1 | 10/2001 |
| WO | 01/89383 A2 | 11/2001 |
| WO | 02/056769 A1 | 7/2002 |
| WO | 03/088835 A2 | 10/2003 |

OTHER PUBLICATIONS

Critical Reviews in Bioengineering, 1990.
Final Office Action mailed Mar. 11, 2009 in related U.S. Appl. No. 10/835,094.
Ginsberg, "An Over of Minimally Invasive Technologies", Clinical Chemistry, 1992, vol./Issue No. 38 (9), pp. 1596-1600, Becton Dickinson and Co.
Janle-Swain et al., "Use of a Capillary Filtrate Collector for Monitoring Glucose in Diabetics", ASAIO Journal, 1987, pp. 336-340, J.B. Lippincott Co.
JP 2000-152923 A English Abstract.
JP 2001-095787 A English Abstract.
JP H02-170388 A English Abstract.
JP H06-004150 A English Abstract.
Kayashima et al., "Suction Effusion Fluid from Skin and Constituent Analysis: New Candidate for Interstitial Fluid", American Journal of Physiology, 1992, vol./Issue No. 263 (5), pp. H1623-H1627, American Physiological Society.
Office Action from United States Patent Office dated Oct. 5, 2007, U.S. Appl. No. 10/165,102, filed Jun. 7, 2002, First Named Inventor: Perez, Devices and Methods for the Expression of Bodily Fluids From an Incision.
Turner et al., "Diabetes Mellitus: Biosensors for Research and Management", Biosensors, 1985, vol./Issue No. 1 (1), pp. 85-115, Elsevier Applied Science Publishers, UK.
U.S. Appl. No. 10/607,347 Office Action mailed Sep. 2, 2009.
U.S. Appl. No. 10/753,973 Office Action mailed Jul. 28, 2009.
U.S. Appl. No. 11/353,849 Office Action mailed Feb. 2, 2009.
U.S. Appl. No. 10/753,973 to Duchon et al., Office Action mailed Jan. 12, 2010.
Ash et al., "A Subcutaneous Capillary Filtrate Collector for Measurement of Blood Chemistries", Ash et al., ASAIO Journal, pp. M699-M705, issue/vol. 39 (3), J.B. Lippincott Co.
U.S. Appl. No. 13/462,902 to Douglas, Office Action mailed May 16, 2013.
U.S. Appl. No. 13/462,902 to Douglas, Office Action mailed Oct. 16, 2013.
U.S. Appl. No. 13/561,672 to Douglas, Office Action mailed May 6, 2013.

* cited by examiner

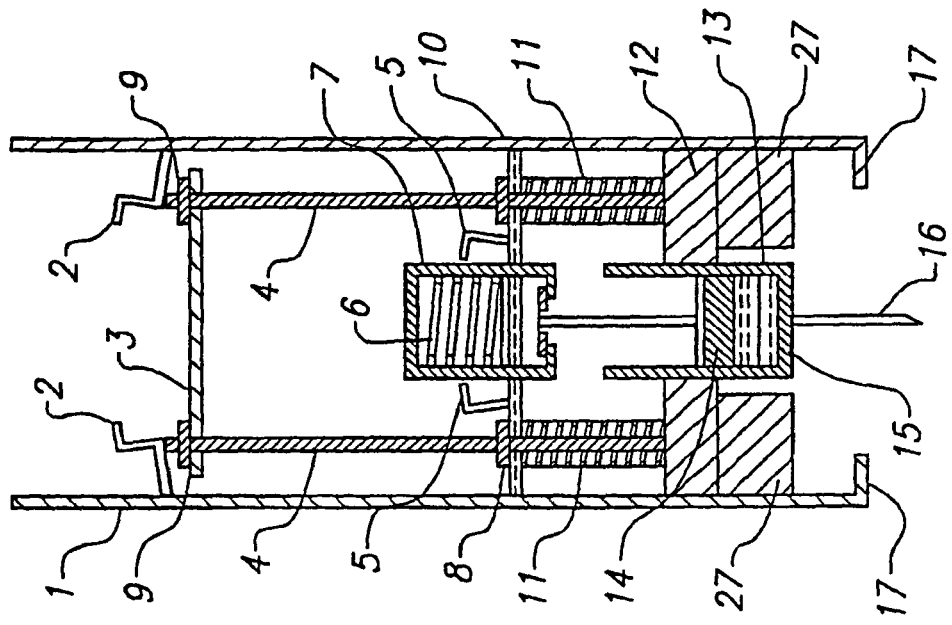
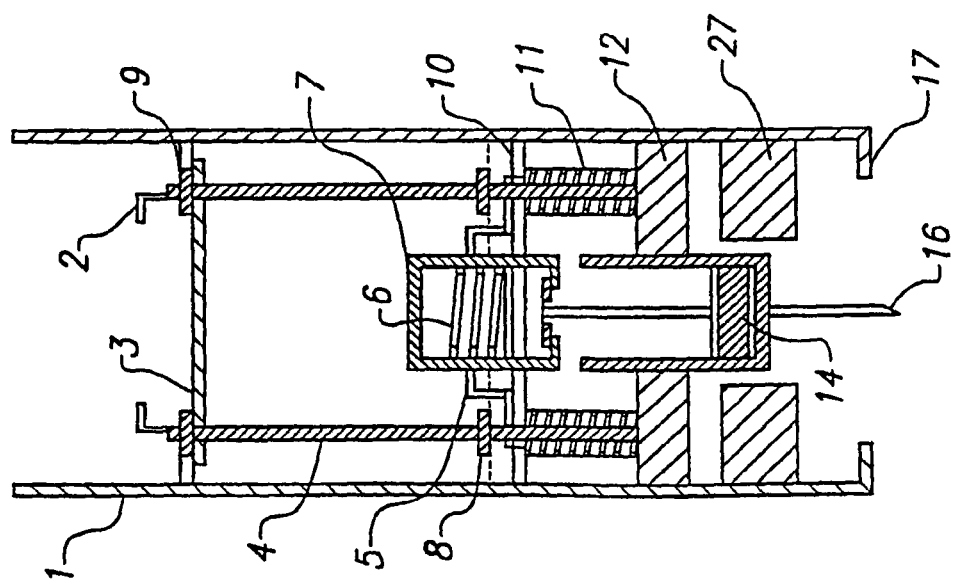

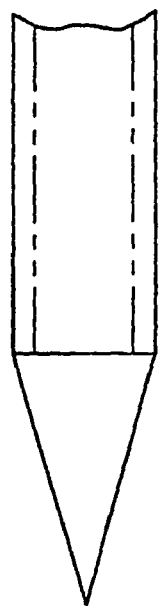
FIG. 5A        FIG. 5B
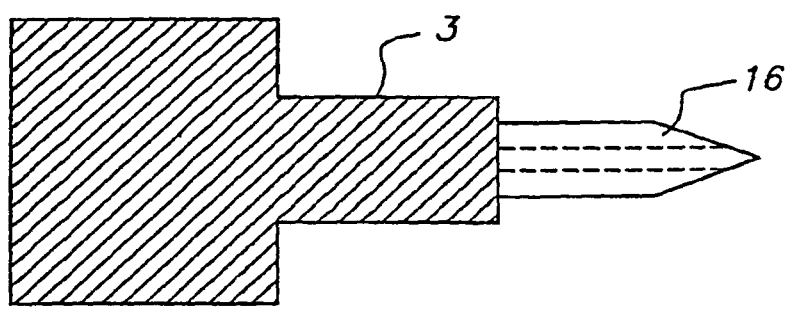
FIG. 6A
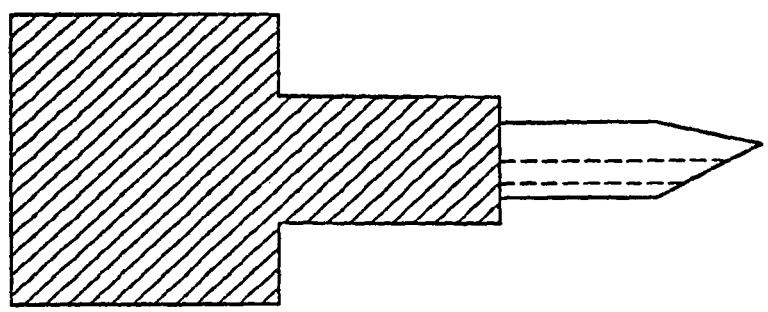
FIG. 6B

BLOOD AND INTERSTITIAL FLUID SAMPLING DEVICE

This application is a divisional of U.S. application Ser. No. 10/835,094, filed Apr. 29, 2004, now U.S. Pat. No. 7,666,150 which is a continuation of application Ser. No. 09/988,799, filed Nov. 20, 2001, now U.S. Pat. No. 6,793,633, which is a continuation of application Ser. No. 09/180,839, filed May 10, 1999, now U.S. Pat. No. 6,332,871, which was the National Stage of International Application No. PCT/US97/08762, filed May 16, 1997, which claims the benefit of U.S. Provisional Application No. 60/017,133, filed May 17, 1996, the entirety of which are hereby incorporated by reference.

FIELD OF THE INVENTION

The present invention relates to devices and methods for obtaining samples of blood and other fluids from the body for analysis or processing.

BACKGROUND OF THE INVENTION

Many medical procedures in use today require a relatively small sample of blood, in the range of 5-50 µL. It is more cost effective and less traumatic to the patient to obtain such a sample by lancing or piercing the skin at a selected location, such as the finger, to enable the collection of 1 or 2 drops of blood, than by using a phlebotomist to draw a tube of venous blood. With the advent of home use tests such as self monitoring of blood glucose, there is a requirement for a simple procedure which can be performed in any setting by a person needing to test.

Lancets in conventional use generally have a rigid body and a sterile needle which protrudes from one end. The lancet may be used to pierce the skin, thereby enabling the collection of a blood sample from the opening created. The blood is transferred to a test device or collection device. Blood is most commonly taken from the fingertips, where the supply is generally excellent. However, the nerve density in this region causes significant pain in many patients. Sampling of alternate site, such as earlobes and limbs, is sometimes practiced to access sites which are less sensitive. These sites are also less likely to provide excellent blood samples and make blood transfer directly to test devices difficult.

Repeated lancing in limited surface areas (such as fingertips) results in callous formation. This leads to increased difficulty in drawing blood and increased pain.

To reduce the anxiety of piercing the skin and the associated pain, many spring loaded devices have been developed. The following two patents are representative of the devices which were developed in the 1980s for use with home diagnostic test products.

U.S. Pat. No. 4,503,856, Cornell et al., describes a spring loaded lancet injector. The reusable device interfaces with a disposable lancet. The lancet holder may be latched in a retracted position. When the user contacts a release, a spring causes the lancet to pierce the skin at high speed and then retract. The speed is important to reduce the pain associated with the puncture.

U.S. Pat. No. 4,517,978, Levin et al., describes a blood sampling instrument. This device, which is also spring loaded, uses a standard disposable lancet. The design enables easy and accurate positioning against a fingertip so the impact site can be readily determined. After the lancet pierces the skin, a bounce back spring retracts the lancet to a safe position within the device.

In institutional settings, it is often desirable to collect the sample from the patient and then introduce the sample to a test device in a controlled fashion. Some blood glucose monitoring systems, for example, require that the blood sample be applied to a test device which is in contact with a test instrument. In such situations, bringing the finger of a patient directly to the test device poses some risk of contamination from blood of a previous patient. With such systems, particularly in hospital settings, it is common to lance a patient, collect a sample in a micropipette via capillary action and then deliver the sample from the pipette to the test device.

U.S. Pat. No. 4,920,977, Haynes, describes a blood collection assembly with lancet and microcollection tube. This device incorporates a lancet and collection container in a single device. The lancing and collecting are two separate activities, but the device is a convenient single disposable unit for situations when sample collection prior to use is desirable. Similar devices are disclosed in Sarrine, U.S. Pat. No. 4,360,016, and O'Brien, U.S. Pat. No. 4,9249,879.

U.S. Pat. Nos. 4,850,973 and 4,858,607, Jordan et al., disclose a combination device which may be alternatively used as a syringe-type injection device and a lancing device with disposable solid needle lancet, depending on configuration.

U.S. Pat. No. 5,318,584, Lange et al., describes a blood lancet device for withdrawing blood for diagnostic purposes. This invention uses a rotary/sliding transmission system to reduce the pain of lancing. The puncture depth is easily and precisely adjustable by the user.

Suzuki et al., U.S. Pat. No. 5,368,047, Dombrowski, U.S. Pat. No. 4,654,513 and Ishibashi et al., U.S. Pat. No. 5,320,607, all describe suction-type blood samplers. These devices develop suction between the lancing site and the end of the device when the lancet holding mechanism withdraws after piercing the skin. A flexible gasket around the end of the device helps seal the end around the puncture site until adequate sample is drawn from the puncture site or the user pulls back on the device.

U.S. Pat. No. 4,637,403, Garcia et al, and U.S. Pat. No. 5,217,480, Haber et al, disclose combination lancing and blood collection devices which use a diaphragm to create a vacuum over the wound site.

International Application Publication Number WO 95/10223, Erickson et al, describes a means of collecting and measuring body fluids. This system uses a disposable lancing and suction device with a spacer member which compresses the skin around the lance/needle.

Single use devices have also been developed for single use tests, i.e. home cholesterol testing, and for institutional use to eliminate cross-patient contamination multi-patient use. Crossman et al, U.S. Pat. No. 4,869,249, and Swierczek, U.S. Pat. No. 5,402,798, also disclose disposable, single, use lancing devices.

Even with the many improvements which have been made, the pain associated with lancing remains a significant issue for many patients. The need for blood sampling and the fear of the associated pain is also a major obstacle for the millions of diagnosed diabetics, who do not adequately monitor their blood glucose due to the pain involved. Moreover, lancing to obtain a blood sample for other diagnostic applications is becoming more commonplace, and a less painful, minimally invasive device is needed to enhance those applications and make those technologies more acceptable.

An object of the present invention is to provide a device and a method for obtaining a sample of bodily fluid through the skin which is virtually pain free and minimally invasive.

Another object of this invention is to provide a method which can result in a sample of either blood or interstitial fluid, depending on the sample site and the penetration depth utilized. While there are no commercially available devices utilizing interstitial fluid (ISF) at this time, there are active efforts to establish the correlation of analytes, such as glucose, in ISF compared to whole blood. If ISF could be readily obtained and correlation is established, ISF may be preferable as a sample since there is no interference of red blood cells or hematocrit adjustment required.

Another object of this invention is to provide a method which can draw a small but adjustable sample, i.e. 3 µL for one test device and 8 µL for another test device, as appropriate.

Another object of this invention is to provide a method by which the drawn sample is collected and may be easily presented to a testing device, regardless of the location of the sample site on the body. This approach helps with infection control in that multiple patients are not brought in contact with a single test instrument; only the sampling device with a disposable patient-contact portion is brought to the test instrument. Alternatively, the disposable portion of a test device may be physically coupled with the sampler so the sample can be brought directly into the test device during sampling. The test device may then be read in a test instrument if appropriate or the testing system can be integrated into the sampler and the test device can provide direct results displayed for the patient.

It is a further object of the invention is to provide a device for minimally invasive sampling comprising a reusable sampler and disposable sample collection.

SUMMARY OF THE INVENTION

In one aspect, the present invention relates to a device which uses mechanical motion to pierce the skin, and a mechanical kneading or oscillation to produce a sample of fluid from the body and may employ a back pressure or vacuum to collect a small fluid sample into the device. More specifically, the present invention comprises a reusable sampling device and a disposable piercing/collecting apparatus. The device may also employ a back pressure, capillary or vacuum to collect a small fluid sample into the piercing/collecting apparatus that may later be discharged to deliver the collected sample to a test device or other appropriate vessel. The system may alternately be used to deliver the sample to an integral disposable test device, without collecting and separately dispensing the body fluid sample.

A method aspect of this invention involves piercing of the skin at a rapid rate (to minimize pain), with a needle (which minimizes the trauma and pressure-associated pain response which occurs with a traditional lancet). The skin is kept taut during the lancing to allow accurate and repeatable penetration of the needle into the skin. After piercing the skin, the needle is withdrawn from the wound and the surrounding area kneaded by ultrasonic action, piezoelectric or mechanical oscillation or squeegee motion to stimulate the blood flow into and from the wound. Additionally heat, electrical potential or friction can be used to stimulate additional flow of the body fluid. This fluid or blood flow can also be stimulated by ultrasonic vibration of the skin surrounding the wound. In an alternate embodiment to stimulate blood flow, the needle remains in the wound for a period of time, with either slow mechanical vibration or rotation of the needle, ultrasonic, or piezoelectric oscillation of the needle, to keep the wound open for blood to pool. After the area has been stimulated and the blood wells up in the wound, a capillary, syringe or pumping system is used to draw microliter samples from the patient. Suction is applied to the needle or the suction tube through either peristalsis, convection (application of heat to a capillary tube) or by the piston of a small microsyringe. The piston is pulled back into the sampler device with spring action, generating a vacuum in the barrel of the microsyringe and quickly drawing fluid from the body through the needle or the suction tube into the barrel to normalize the pressure differential. The piston or suction device then can be reversed to dispense the collected sample. The system can also use a capillary tube which is used to draw the sample after it has been collected on the skin surface. The capillary tube can then dispense the sample to a desired test or analysis device by applying pressure through the tube or simply contacting the end of the tube and the sample with a surface or material that has sufficient affinity for the fluid to pull the sample from the tube.

The above method and system may be used on various parts of the body. It is particularly appropriate for use on sites other than the fingertips. Although fingertips provide good blood flow, the high density of pain receptors provide for easy access to blood but maximum pain in sampling. The method of this invention actively draws a sample from the body, enabling the use of sampling sites on the body which are inadequate for traditional lancing. Since the method can also provide a mechanism for the easy transfer of the sample, the difficulty of bringing the sample to a test device is eliminated. An important benefit of this system is that the use of alternate sites on the body reduces the accompanying pain sensation and encourages more frequent use as needed.

While the method may be readily used to obtain a blood sample in a minimally invasive fashion, a sample of interstitial fluid may similarly be obtained, generally utilizing a less deep puncture in sites with lower blood flow. This will become more important as tests are developed which can utilize ISF samples, which may be preferred compared to blood.

This invention provides a device and method for lancing a patient and virtually simultaneously producing and collecting the fluid sample, which may be transferred to a test device. A preferred device of the present invention comprises a blood collection system including a lancing needle, drive mechanism, kneading or vibration mechanism and optional suction system and sample ejection mechanism. The device is preferably sized to be hand-held in one hand and operable with one hand. The device can optionally contain integral testing or analysis component for receiving the sample and providing testing or analysis indication or readout for the user.

The lancing needle and firing mechanism designed to create a wound which will both provide an adequate sample but which will still close and heal quickly. Wound healing is an especially important consideration for diabetic patients who often have compromised circulatory systems and slow healing processes. The wound must have a geometry which allows for a momentary space in which blood can fill, taking into account the elastic nature of the skin tissues. Careful consideration must be given to these geometries or the dermis will seal around the lancing needle tip, precluding the drawing of a sample through the tip. In a preferred embodiment a needle is used in combination with a flexible collar and outer tube to spread the wound so blood can pool. Alternatively a multiple needle lancing device can be used to generate a wound which disrupts multiple capillary areas to quickly provide large sample size, but the smaller multiple wounds, can heal more easily.

In an alternate embodiment, the needle/lance is withdrawn from the wound, and the area surrounding the wound is massaged or stimulated to prevent it from closing and to promote the flow of body fluids and or blood to the wound and to the surface of the skin.

Devices according to this invention create a lancing motion which cuts into the small but plentiful capillaries in the superficial vascular plexus under the epidermis. This vascularized region starts at a depth of 0.3-0.6 mm from the surface of the skin in many accessible areas throughout the body (forearm, thigh, abdomen, palm). Blood is in plentiful supply in this region of the skin, and healing of small wounds is not problematic. However, bringing a sizable drop of blood to the surface is more problematic than with a finger stick. A finger stick is typically massaged to increase momentary blood flow. This invention provides a system for mechanically massaging a lance site at other body locations by several different approaches, including oscillating an annular ring surrounding the wound to pump the blood surrounding the wound into the wound for extraction by a needle or capillary tube or oscillating paddles or other members adjacent the wound to achieve the desired blood flow. Further, bringing a drop of blood from the skin in other regions of the body, e.g., the thigh, to a small area on a test device is very difficult. An alternate embodiment of the present invention works with the needle remaining in the wound and the needle being mechanically manipulated to promote the formation of a sample of body fluid in the wound.

The needle may be vibrated in any desired and effective motion, including an up and down motion, a side to side motion, a circular motion, a rotation motion or any combination thereof. This creates a momentary opening in which the blood can fill while the device draws the blood through the needle into the disposable sample collection chamber. The vibration of the needle may occur across a broad range, from 30 cycles per minute up to 1000 cycles per minute or more. This slight vibration does not measurably increase the sensation felt by the patient, particularly when a short duration time is used, but does markedly increase the sample volume which may be easily withdrawn from a given wound and the rate at which the sample volume is produced from the wound. The oscillation can cause the needle to move up to 2-3 mm per cycle. The optimal needle oscillation is less than 1.5 mm, with about 0.5 mm preferred based on current investigations. Oscillating or rotating the needle from 30 cycles per minute up to 1000 cycles per minute or more holds the wound open and prevents it from closing and stopping sample collection and provides sample collection in a shorter amount of time.

Lancing conventionally occurs at a 90 degree angle (perpendicular) to the skin surface. However, we have found that the lancing member may puncture significantly more capillaries if the lancing is performed on a angle. At a too shallow angle, no significant depth of penetration is achieved. Lancing at an incident angle of 15-90 degrees to the surface of the skin is effective, with shallower angles producing greater blood flow.

The device and system of this invention can further enhance blood flow by massaging the site prior to lancing, as well as by massaging the area adjacent the lancing cite while the lancing member is in the wound and after it is removed from the wound, as well as during sample collection, as described above. Alternate methods can use a wiper to rub across or vibrate the skin or can apply heat to the skin to increase the blood flow to the sampling site.

In another alternate configuration, the lancing needle may be withdrawn very slightly from the point of maximum penetration to create an opening in which blood can pool before being suctioned through the device. This can be accomplished with a double stop system which stops the needle at maximum penetration then stops the retraction of the needle at partial but not full retraction. The area surrounding the wound can be kneaded or massaged by optional movable members mechanical to stimulate blood flow to the wound and increase the sample size and the rate of production of the sample. The mechanical motion can displace the area around the wound from 0.05 to 8 mm, with 1-5 mm being preferred based on current investigations. A wiper device can be used in the aspect which rubs the skin to increase the blood flow to the wound by stimulating the capillaries.

The mechanical stimulation of the wound can be accomplished by different methods or motions and members. An annular ring or other polygon or blade or paddle members may be oscillated around the wound by piezoelectric, ultrasonic, solenoid/coil, motor and cam or other methods apparent to one skilled in the art. Mechanical oscillation in the range of 2 to 1000 cycles per minute may be employed, with 10 to 400 cycles being preferred. Ultrasonic vibration has been effective at a frequency as high as 40 kHz. Alternately, the device may employ a blade or squeegee type of stimulator which kneads the site with horizontal or a combination of horizontal and vertical action and promotes blood flow to the wound. The squeegee may act on the wound area 2 to 200 times per minute, with 60 times per minute preferred based on current investigations. Additionally, the needle may be vibrated ultrasonically, with or without the kneading or massaging action adjacent the wound. The ultrasonic vibration can cover the range of ultrasonic frequencies depending on the sampling area and whether the needle or the stimulation device is being activated.

In another aspect of this invention the lancing member is contained a multi-chambered or multi-channelled capillary disposable member wherein one chamber contains the lancing member and an adjacent chamber is adapted to receive the blood or fluid exiting the wound. The multi-chambered capillary disposable can be made from any suitable material, and installed in the sampler so that it is positioned in the appropriate position relative to the wound created to permit collection of the sample. The lancing device is driven into the skin and withdrawn by the secondary retraction springs after reaching the limit stops. After withdrawal of the lancing member, the stimulator ring or other polygon shape is oscillated by one of the various methods to pump blood from the capillaries adjacent to the wound. The sampling device of this aspect of the invention has stop mechanisms to limit the penetration of the lancing member and sample duration system which sets the time of the sample collection. The lancing guide chamber can be formed a variety of ways and one skilled in the art can reconfigure it to create alternate embodiments.

In another aspect similar to the above, the lancing member can be contained within a single capillary tube and adapted to extend from the end of the tube to create the wound. The lancing member then retracts a sufficient distance inside the capillary to allow the desired sample to be collection in the end of the same capillary tube in the space below the retracted lancing member. In such an embodiment the lancing member can be vibrated in the wound before retraction, also as described above.

To achieve the sample collection after withdrawing the needle, a stimulator ring can be used to pump the sample from the surrounding capillaries through the wound opening. The stimulator ring is designed to keep the skin taut to allow better penetration of the skin during lancing and help keep the wound open during pumping. It can be oscillated appropriately to insure that enough sample is pumped from the local capillaries. The time or number of cycles varies by individual and location being sampled. To achieve a variable sample time either of the following methods may be used. A sensor can be built into the sampler which senses the blood in the collection chamber or device. When an adequate sample level (which may be adjustable) is reached, the stimulation mechanism is turned off. A second method is to have a patient definable input which sets the time duration for the test or the number of cycles for the stimulation ring. Additional stimulator motions can be employed to promote the extraction of bodily fluids. These include sinusoidal motion, wobbling, kneading or peristaltic motion. An alternate stimulator device can be designed with an inner and outer ring which will alternate creating a peristaltic pumping motion on the capillaries surrounding the wound. Another alternate stimulator device uses a spiral spring that can be compressed flat to emulate multiple pumping rings. As will be apparent, various configurations of multiple stimulator rings, paddles, or other members, used in various rhythms and orders of movement can be employed in the present invention. The stimulator ring or member can be heated in order to heat the skin to increase the capillary volume flow to and out of the wound. In addition, the housing or case of the device or other components of the device can be heated to provide heating of the skin.

In another aspect of the invention a diffused laser may be used to penetrated to the superficial vascular plexus and a capillary tube may be used to collect the sample. A lens may be used to diffuse the laser so that it does not create a large wound or damage large areas of skin and tissue. A minimum wound size is important to enable rapid healing. The capillary collection tube can use a suction generator to draw the sample up the tube and can also utilize an optional stimulator ring to pump the blood from the adjacent capillary beds.

In another aspect of the invention the lancing can be accomplished by a pulse of a fluid under high pressure such as a liquid or a compressed gas. In addition the compressed gas can be directed, at lower pressure, to the skin surface to massage the skin before lancing, during lancing and/or during sample collection. Pulsing the compressed gas against the skin at desired pressures, patterns and intervals, including sequential pattern across the surface of the skin, can provide the desired stimulation of the blood flow into and from the wound. The pulse of compressed gas used to perform the lancing and opening of the wound can be a single pulse or multiple pulses, can be directed through a capillary sample collection tube, and/or can be applied vertically to the skin surface or at an angle, as described above for other lancing members, to achieve puncturing the maximum capillaries in the skin and provide the sample collection in a short period of time.

In another aspect of the invention an off meter test device is used with a sampler of this invention to provide an integrated sampling and testing device. This device can be used by the patient to essentially simultaneously draw a sample and test for the presence or concentration of an analyte in a body fluid. The sample can be taken from an alternate location other than the fingertips with the device of this invention. To accomplish this it is critical to the test to provide a mechanism to stimulate the wound and or the surrounding area to provide an adequate sample for the test device. This stimulation can be accomplished by manipulating the needle or the area of skin surrounding the wound as described above. A combination of the two methods can be employed to increase the volume and/or decrease the sampling time. The sample is introduced directly into a test device or testing area rather than being collected and subsequently dispensed.

In another aspect, this invention also provides a method of determining the correct sample size prior to transferring or testing. Different methods can be used to sense the volume and/or presence of the sample. One system uses two contacts to sense the presence and/or volume of a sample. The body fluid either is drawn up a tube or wells up on the surface of the skin where it creates a short between two contacts which signal that the proper sample has been drawn. An alternate system uses an LED and receiver. When the sample rises to the level where it blocks the LED from the receiver the proper sample has been drawn. Other optically activated or contact activated systems can be used in this aspect of the invention.

In another aspect, this invention also provides a method of making a unit with a disposable section to limit biohazard cross contamination.

In another aspect, this invention provides a bell shape capillary tube. The capillary tube wicks the sample up the tube until it reaches the transition of the bulb. The bulb is then depressed to expel the sample or a known volume of the sample to a desired location, such as a test strip or device for analysis. The bell shape can be designed as a cone and the sample is wicked up the cone and dispensed by reversing the cone and expelling the sample by capillary action onto the test device.

In an alternate embodiment the device of this invention lances and stimulates the area, creating a drop of sample fluid, which is collected on or transferred directly to a test device by applying the test device to the drop.

In another aspect, this invention can also include an auto-injection device. A preloaded tip may be placed into the barrel. The trigger and spring system can be designed to deliver the sample from the syringe rather than to collect a sample into the syringe. One who is skilled in the art could readily reconfigure the mechanism described to inject a sample. Moreover, the device may have dual function of collecting a sample while simultaneously or sequentially injecting a sample, which can be in response to a test performed in the device on the sample collected.

BRIEF DESCRIPTION OF DRAWINGS

FIG. 2A and FIG. 2B are cross section views of a device of this invention in the cocked and the deployed position, respectively.

FIGS. 5A and 5B show front and side views of a replaceable needle with a spade tip design adapted for use in this invention, especially for a moving/rotating needle for holding a wound open during sample collection.

FIGS. 6A and 6B illustrate a front and side view of a disposable needle that has an eccentric passageway for sample collection. The needle can have a luer lock type connection to the sample device of this invention.

DESCRIPTION OF THE INVENTION

Figure 1:
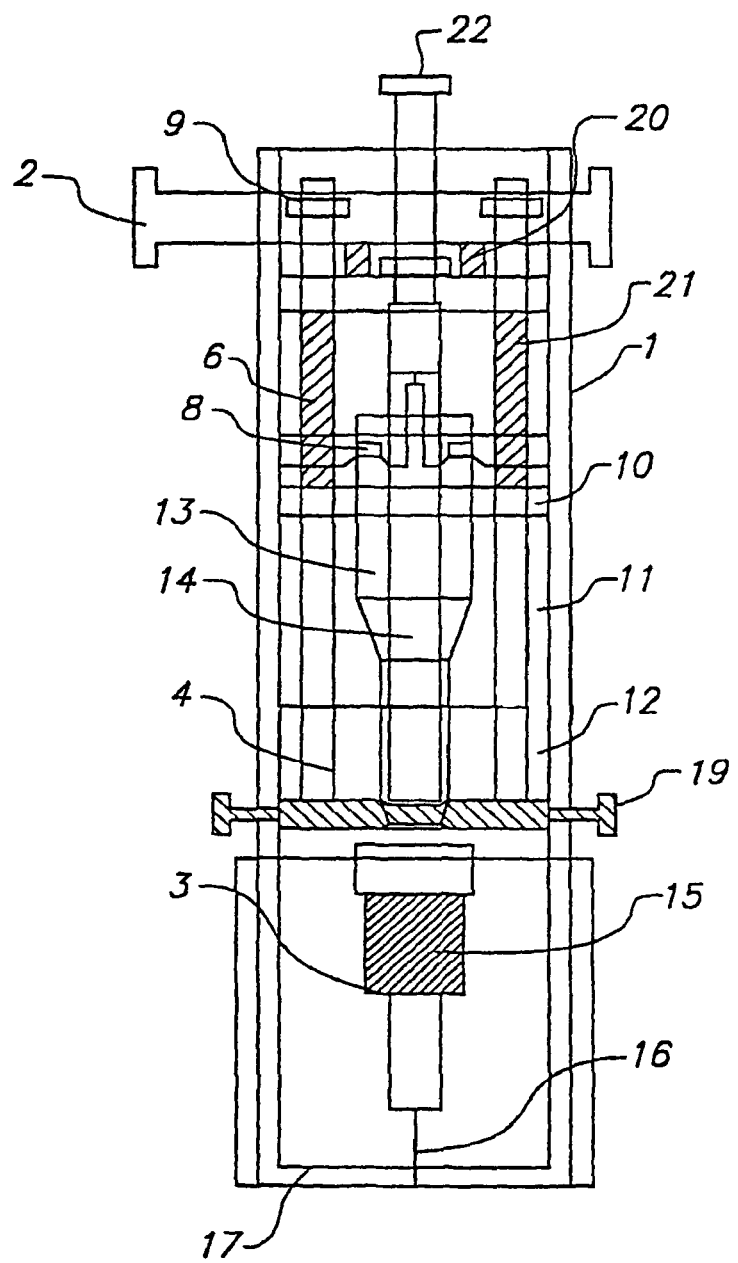
FIG. 1 shows a device of this invention having a double stop mechanism.

FIG. 1 illustrates a minimally invasive sampling device according to the invention. The device is comprised of numerous components which will be more fully described below. The main body 1 supports the various mechanical components housed within the device.

The main body 1 comprises an elongated hollow cylindrical tube with openings at both ends. The sampling needle 16 which is part of the disposable 3 which is capable of being retracted or deployed so that it can protrude beyond the needle guard 17 is positioned at one end. The arming and dispensing plunger 22 protrudes from the other end. The device has a needle guard 17 which permits the loading of the disposable 3. Disposable 3 is attached to the syringe 13 and plunger 14 is released by the suction cam 8.

The syringe 13 is captivated to the drive system by syringe clamp 12 which has the main tie rods 4 anchored to it. The main drive springs 11 are captivated between the syringe clamp 12 and cross support 10 and the tie rods 4 are threaded through them.

The main tie rods 4 have the main cams 9 attached to them and are supported by the activation trigger 2 prior to release. The secondary springs 21 and secondary stops 20 provide a mechanism after activation to pull the needle back out of the wound to permit blood accumulation. When the skin is pierced the secondary springs 20 retract the needle from the wound triggering the suction cam 8 and plunger 14 is released. The arming and dispensing plunger 22 is a dual purpose device. When the patient pulls up, it preloads the drive springs 11. It is latched by pushing in on the activation trigger 2.

The stop and adjustment tabs 19 control the depth of penetration of the needle 16 so that the optimal depth of penetration is reached for a particular sample site. The sample 15 is drawn from the patient when the device has been deployed by releasing the activation trigger 2 and the needle 16 has been retracted from the patient.

The system shown in FIGS. 2A and 2B is comprised of a reusable barrel 1 and associated mechanisms and a sterile disposable 13. The disposable 13 has an ultra fine gauge needle 16 which is imbedded in a cap until the device is readied for use. FIG. 2B shows the device in the deployed state with a sample in disposable 13 and FIG. 2A shows it undeployed.

Main yoke 3 is held by activation triggers 2 which support the main tie rods 4 when the system is undeployed. The system is activated by releasing the activation triggers 2. This releases the main cam 9 which causes the syringe to be deployed by the drive spring 11 which is captured between the cross support 10 and the syringe clamps 12. The needle 16 pierces the skin as a result of these actions and the penetration depth is controlled by stop 27. When the suction cams 8 is released by the secondary trigger 5, the suction spring 6 is released. This drives the suction yoke 7 up slowly due to the damping action of the syringe plunger 14 so a back pressure or vacuum is created in the syringe body. Sample 15 is actively drawn into the syringe.

The sample can be delivered easily and precisely to a test device or other container by pressing down on a button on the top of the sampler. The disposable syringe 13 and needle 16 may be imbedded in the cap in which it was shipped or placed into a Sharps container for safe disposal.

To insure that adequate sample size is collected the needle 16 can be vibrated, oscillated or rotated to keep the wound from closing. The disclosure of FIGS. 3, 4, 4C, 4D, 4E, 4I, 9, 12 and 13 show and describe various alternative motions that can be used to accomplish this.

Another version of this device is also capable of performing as an auto-injection device. A preloaded tip may be placed into the barrel. The trigger and spring system can be designed to deliver the sample from the syringe rather than to collect a sample. One who is skilled in the art could readily reconfigure the mechanism described to inject a sample.

Figure 3:
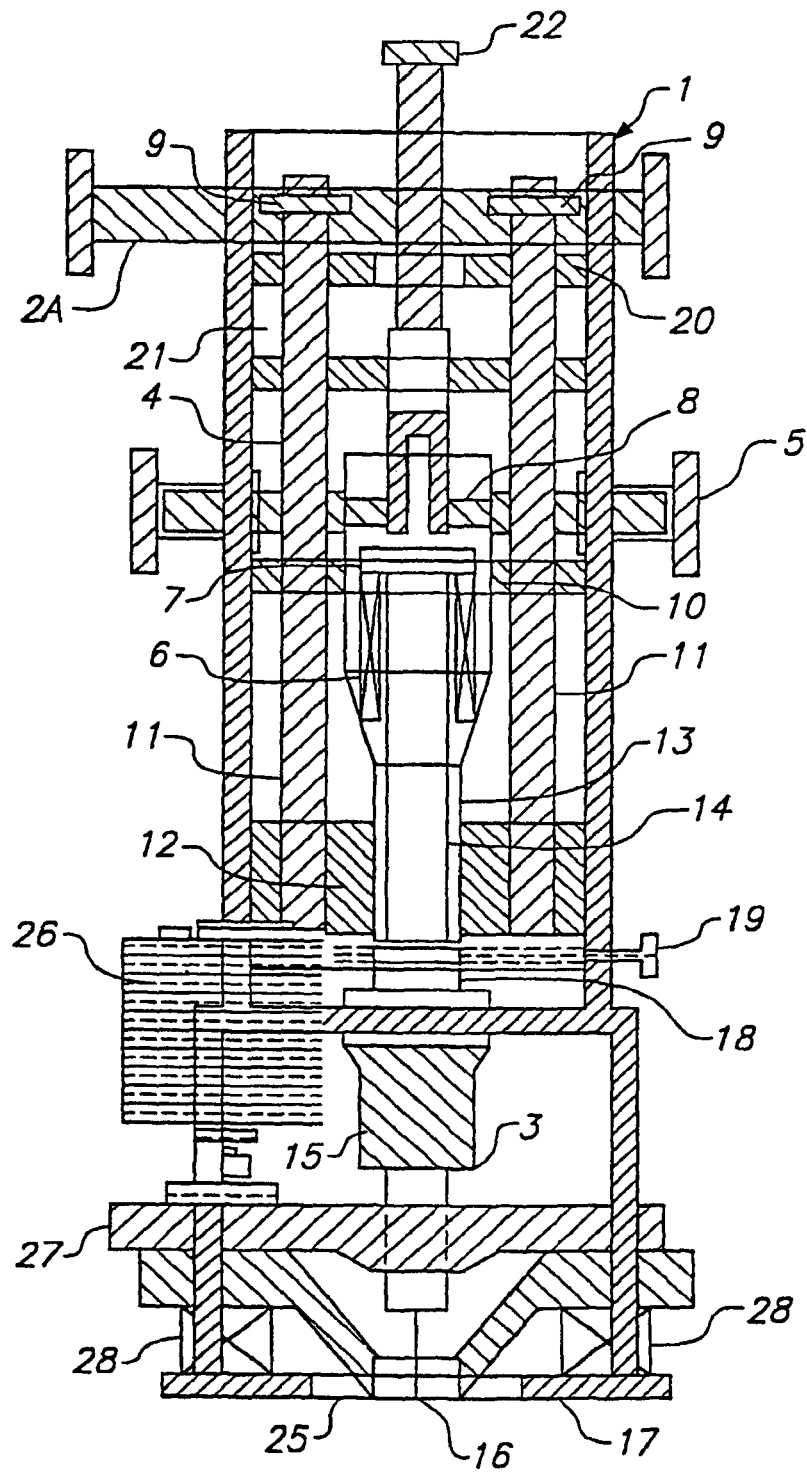
FIG. 3 shows a longitudinal cross section of a device according to this invention having a stimulator member proximate to the lancet or needle.

FIG. 3 illustrates a minimally invasive sampling device according to the invention. The device is comprised of numerous components which will be more fully described below. The main body 1 supports the various mechanical components housed within the device.

The main body 1 comprises an elongated hollow cylindrical tube with openings at both ends. The sampling needle 16 which is part of the disposable 3 which is capable of being retracted or deployed so that it can protrude beyond the needle guard 17 is positioned at one end. The arming and dispensing plunger 22 protrudes from the other end. The device has a needle guard 17 which can be slid up and down main body 1 by the patient to permit the loading of the disposable 3. Disposable 3 is attached to the syringe 13 by the tip adapter 18. The internal parts of the syringe 13 are the plunger 14 which is activated by the suction spring 6 and the suction yoke 7. The plunger is released when the suction cam 8 is released by the secondary trigger 5.

The syringe 13 is captivated to the drive system by syringe clamp 12 which has the main tie rods 4 anchored to it. The main drive springs 11 are captivated between the syringe clamp 12 and cross support 10 and the tie rods 4 are threaded through them.

The main tie rods 4 have the main cams 9 attached to them and are supported by the activation trigger 2A prior to release. The secondary springs 21 and secondary stops 20 provide a mechanism after activation to pull the needle back out of the wound to permit blood accumulation. When the skin is pierced the secondary springs retract the needle from the wound and initiate the stimulation ring 25 oscillation system 26 and 27 to force blood flow to the wound. The arming and dispensing plunger 22 is a dual purpose device. When the patient pulls up, it preloads the drive springs 11. It is latched by pushing in on the activation trigger 2A.

The stop and adjustment tabs 19 control the depth of penetration of the needle 16 so that the optimal depth of penetration is reached for a particular sample site. The stimulator ring can be deployed during lancing to keep the skin taut, thus allowing more accurate and repeatable penetration of the skin. The sample 15 is drawn from the patient when the device has been deployed by releasing the activation trigger 2 and the needle 16 has been retracted from the patient.

Figure 4:
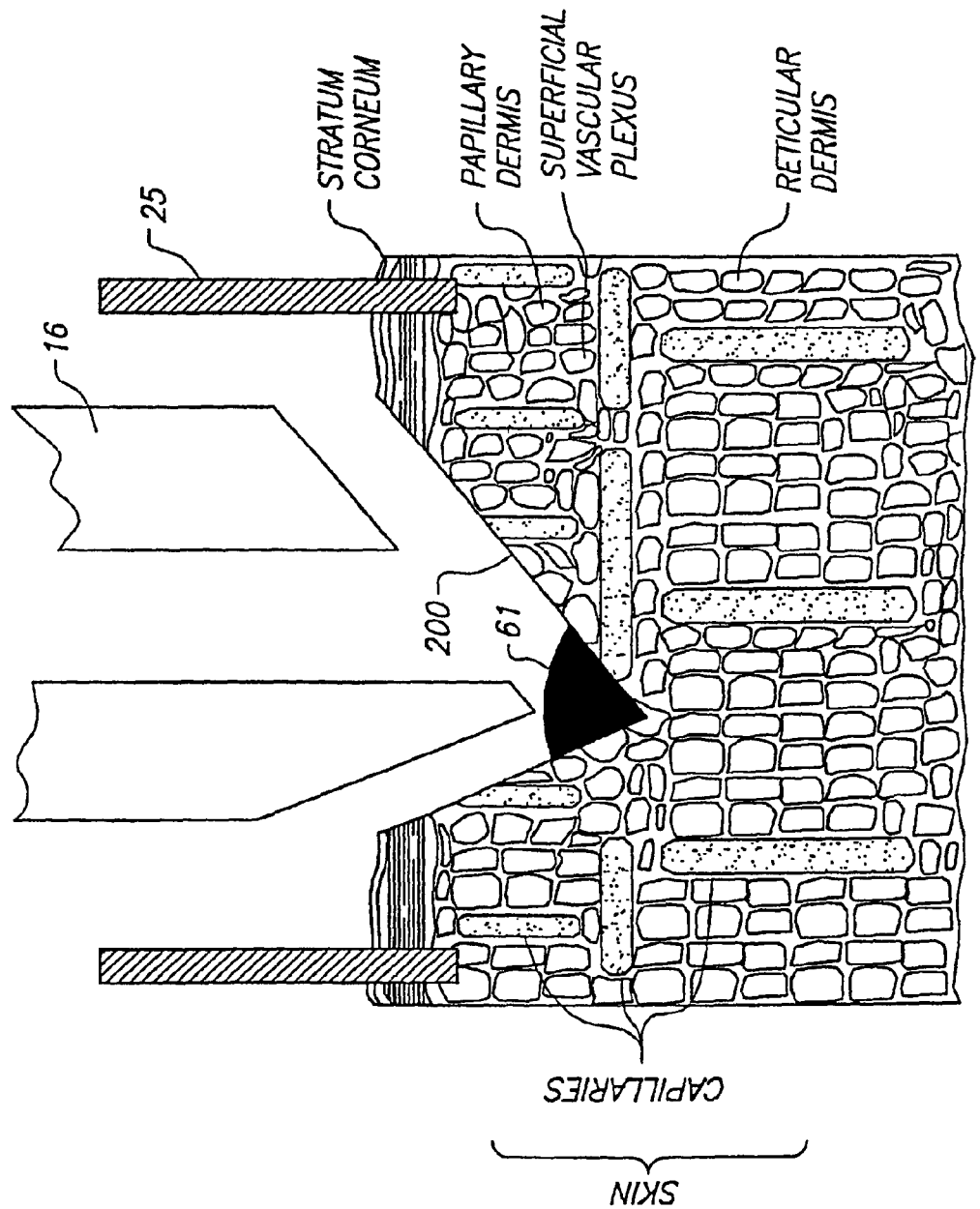
FIG. 4 shows the stimulator member positioned on the skin of the patient adjacent the wound and the lance.
Figure 4A:
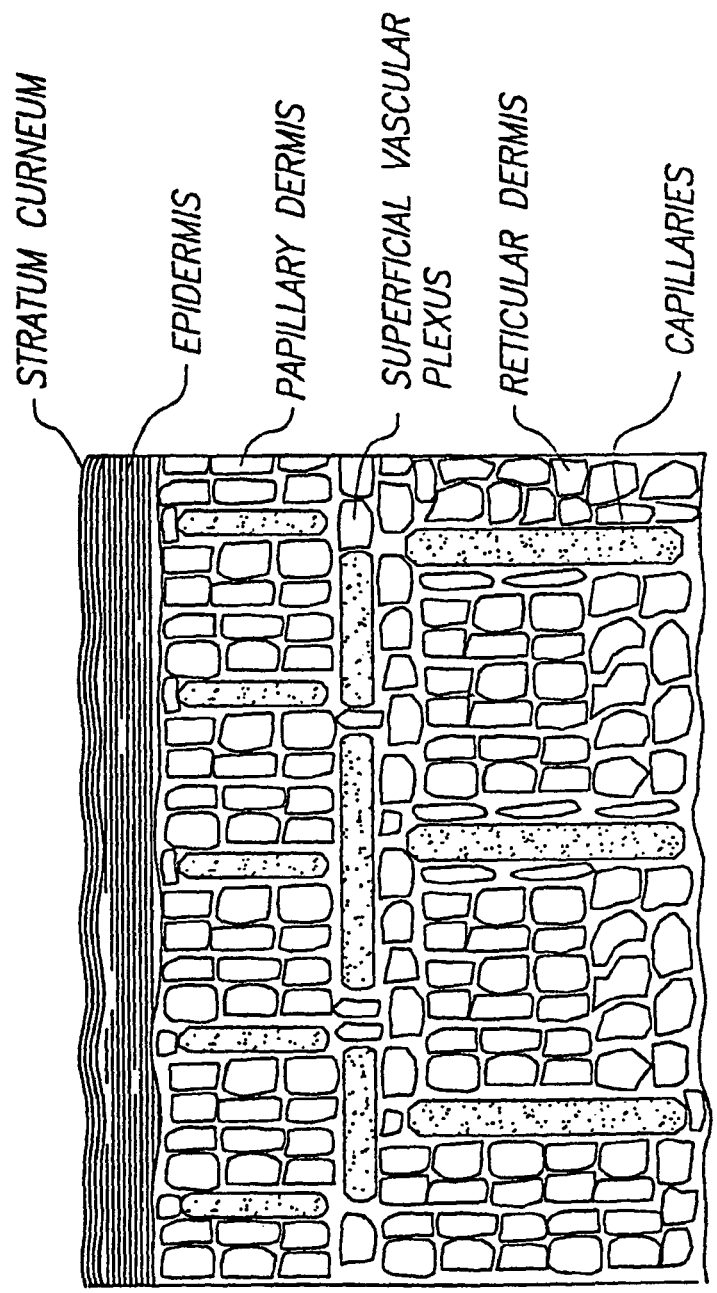
FIG. 4A provides a schematic layout of the skin illustrating where the superficial vascular plexus capillaries are relative to the skin's surface.

FIG. 4 illustrates the relationship of the needle 16, wound 200 and stimulation ring 25. The detail areas of the skin are shown for clarity. The stimulator ring 25 is used to pump the sample of body fluid 61 into wound area 200. A singular stimulation ring 25 is shown in this illustration. However, multiple telescoping rings may be employed to enhance the blood transport.

The stimulation ring can also be formed to with a series of notches to permit the resupply of body fluid to the capillaries when the stimulation ring 25 is retracted from the wound site 200.

In an alternate embodiments the stimulation ring is heated or a secondary motion added to act as a wiper to enhance the flow of body fluid to the wound 200. Other members can be used instead of a ring to provide the stimulation desired.

Figure 4B:
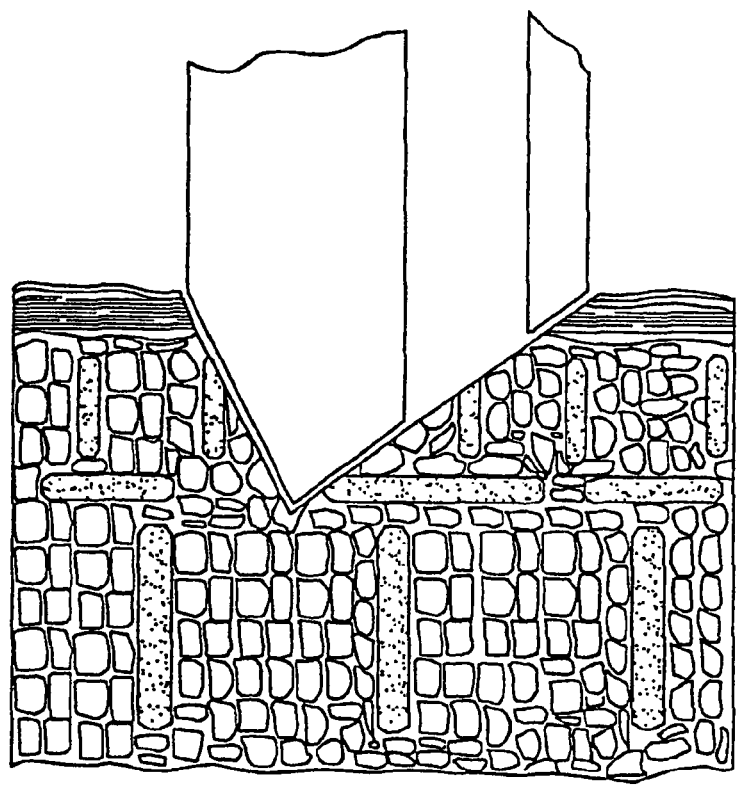
FIG. 4B is a representation of a wound, shown in cross section, which will facilitate the formation of a small pool of blood yet ensure that the skin will fully contract around the wound following sampling to promote healing. The relationship of the wound, needle and the superficial vascular plexus capillaries is also illustrated. In the embodiment shown the capillary is offset in the needle.
Figure 4C:
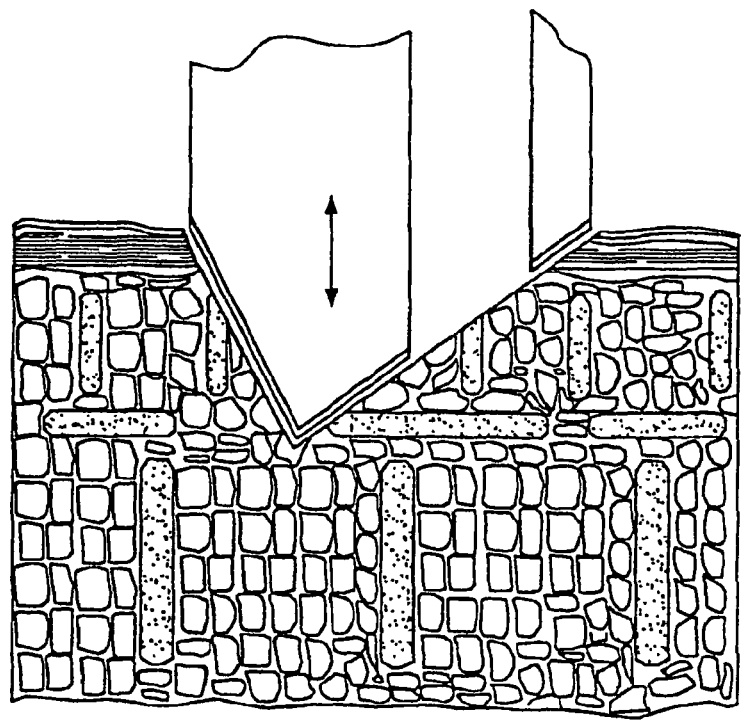
FIGS. 4C and 4D show alternative embodiments in which, to enhance sample collection and minimize the wound size required, the needle may be vibrated mechanically in either an up and down motion as shown in FIG. 4C or a side to side as shown in FIG. 4D.
Figure 4D:
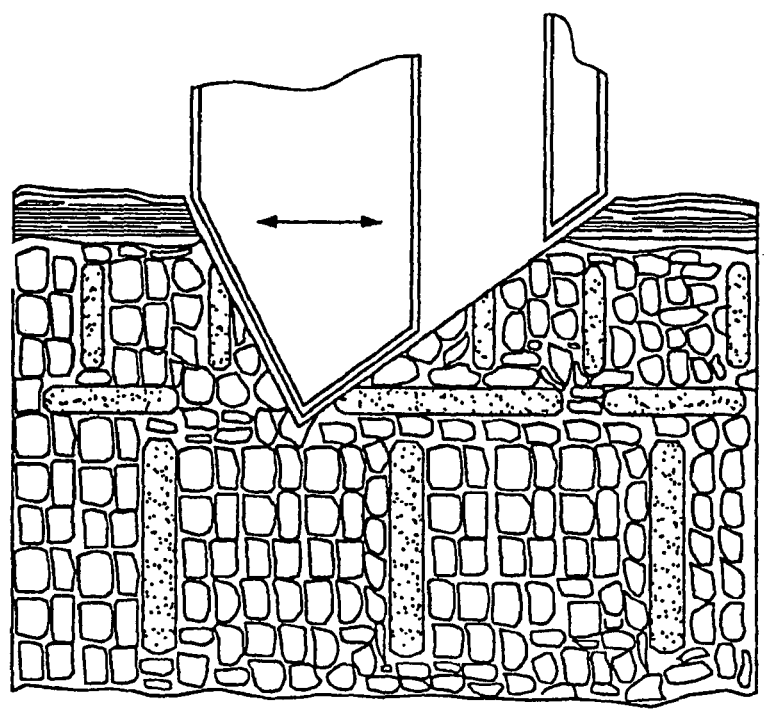
Figure 4E:
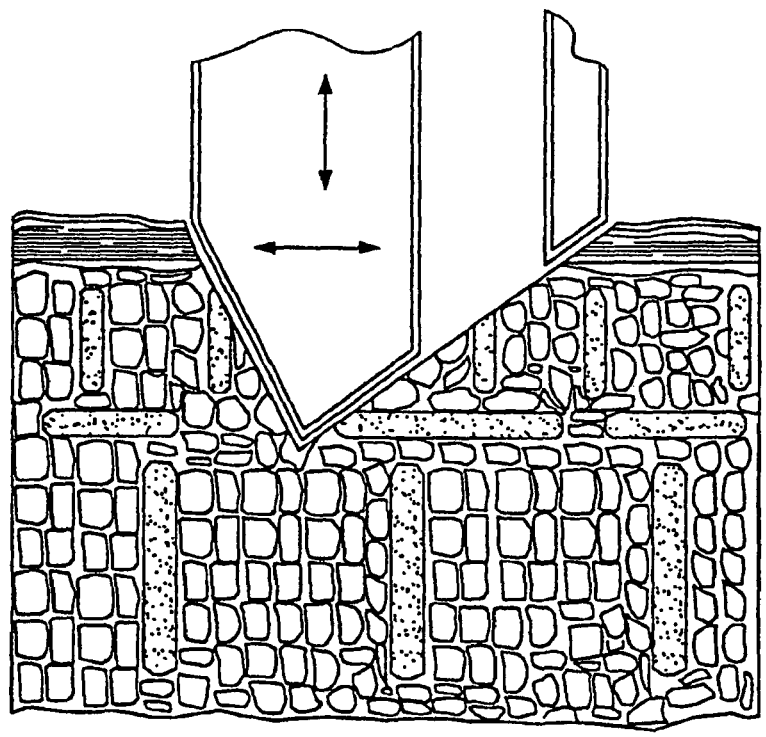
FIG. 4E shows that the needle may be vibrated ultrasonically with or without the kneading or massaging action.

FIGS. 4C, 4D and 4E illustrate that the needle may be vibrated in the desired motion. This creates a momentary opening in which the blood can fill while the device draws the blood through the needle into the disposable sample collection chamber. The vibration of the needle may occur across a broad range, from 30 cycles per minute up to 1000 cycles per minute or more. This slight vibration does not measurably increase the sensation felt by the patient but does markedly increase the sample volume which may be easily withdrawn from a given wound and the rate at which the sample volume is produced from the wound. The oscillation can cause the needle to move up to 2-3 mm per cycle. The optimal needle oscillation is less than 1.5 mm, with about 0.5 mm preferred based on current investigations. Lancing generally occurs at a 90 degree angle (perpendicular) to the skin surface. However, the lancing member may puncture significantly more capillaries if the lancing is performed on a angle. At a very shallow angle, no significant depth of penetration is achieved. Lancing at an incident angle of 15-90 degrees to the surface of the skin is effective, with shallower angles producing greater blood flow. The ultrasonic vibration can cover the range of ultrasonic frequency depending on the sampling area and whether the needle or the stimulation device is being activated.

Figure 4F:
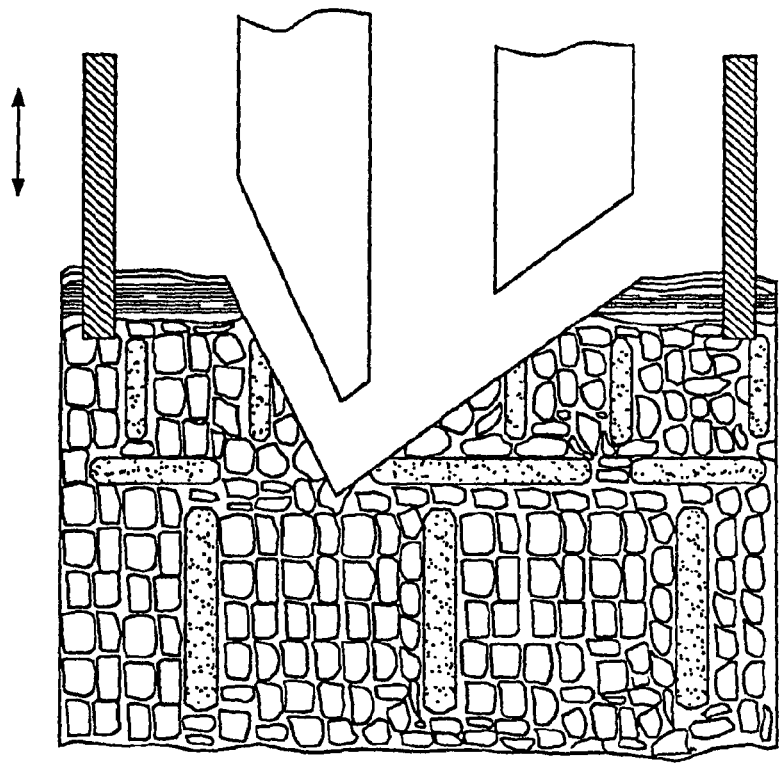
FIGS. 4F and 4G show that the area surrounding the wound can be kneaded by optional mechanical motion to stimulate blood flow to the wound and increase the sample size and the rate of production of the sample.
Figure 4G:
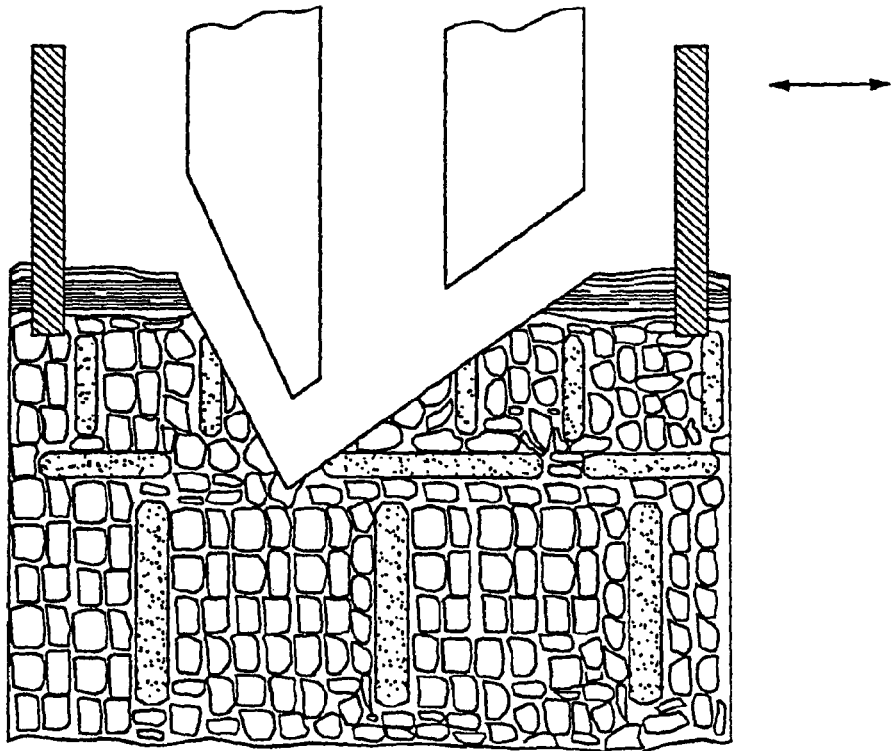

FIGS. 4F and 4G show massaging or kneading the area surrounding the wound. The mechanical motion can displace the area around the wound from 0.05 to 8 mm, with 1-5 mm being preferred based on current investigations. FIG. 4G shows a wiper device which rubs the skin to increase the blood flow to the wound by stimulating the capillaries. This action can also be done by the patient by rubbing the area to increase the blood flow to the sampling site prior to taking a sample. The oscillation can be accomplished via piezoelectric, ultrasonic, or by using a solenoid/coil or a motor and cam. Mechanical oscillation in the range of 2 to 1000 cycles per minute may be employed, with 20 to 200 cycles being preferred. Ultrasonic vibration has been effective at a frequency as high as 40 kHz. FIG. 4F shows an alternate embodiment in which the wound is mechanically stimulated such as by an annular ring which may be oscillated.

Figure 4H:
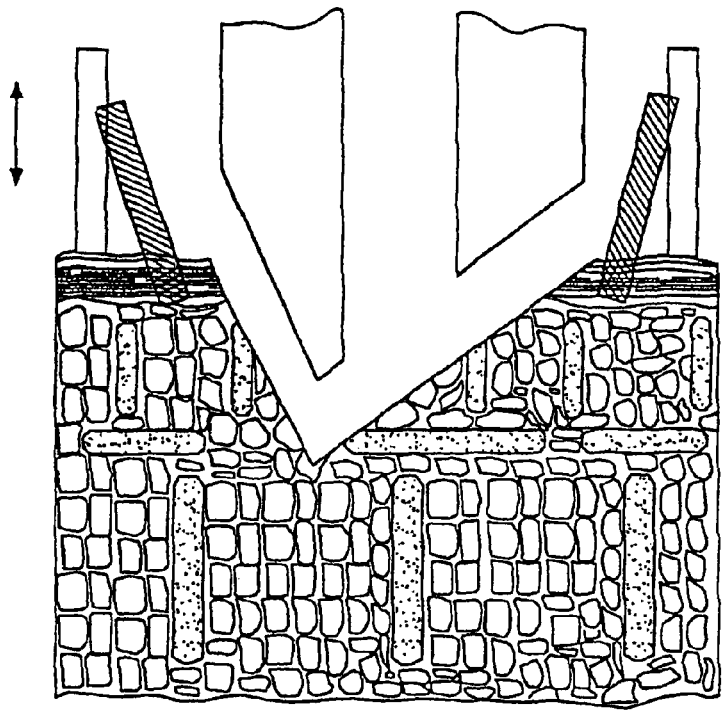
FIG. 4H shows that, alternately, the device may employ a squeegee type of stimulator which kneads the site with horizontal or a combination of horizontal and vertical action and promotes blood flow to the wound.

FIG. 4H shows massaging with a squeegee type of stimulator. Such a squeegee may act on the wound area 2 to 200 times per minute, with 60 times per minute being preferred.

Figure 4I:
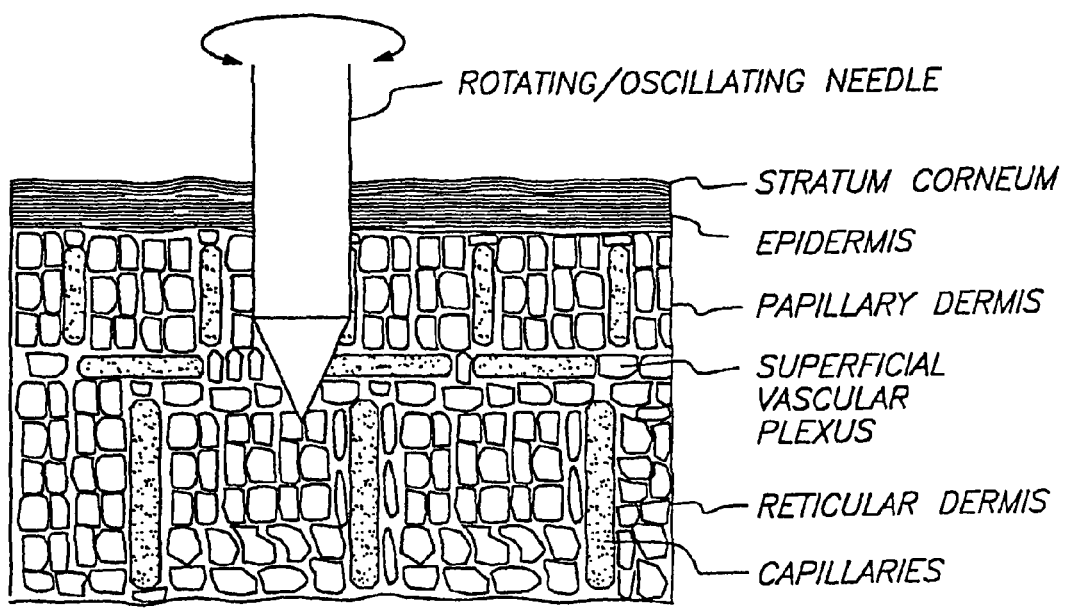
FIG. 4I shows an alternate embodiment in which needle is oscillated or rotated.

FIG. 4I shows rotating or oscillating the needle from 30 cycles per minute up to 1000 cycles per minute or more. This holds the wound open and prevents it from closing and stopping sample collection. This embodiment can employ the needles disclosed herein in FIGS. 4B, 5A, 5B, 6A and 6B, conventional needles or round or flat lancets.

FIGS. 5A and 5B show a spade tip needle/lance profile which is used by the invention to create a void area in the wound. FIGS. 5A and 5B show one needle profile which is useful in implementing this embodiment. The spade end helps create a void area when it is rotated in the small wound.

FIGS. 6A and 6B show an asymmetric needle design to create a wound which can enhance capillary blood collection. Needle 16 is molded to form disposable 3. Another aspect of the invention is the provision of an easily replaceable lancing tip (FIGS. 6A and 6B). The tip must attach to the device simply to facilitate the availability of a fresh, sterile needle for each sample drawn. A wide range of lancet or needle gauges may be used for the tip. Current investigations show that 10 through 32 gauge is acceptable depending on the sampling location. The entire device may also be designed as a single use device. In this configuration, the device would be precocked and would only trigger and dispense once. A new device with a sterile tip would be thus used for each sample drawn. It will be apparent that an alternate disposable can be constructed from a needle and flexible tube. The tube acts as a reservoir for the sample as it is drawn by the applied vacuum. Another capillary type disposable is shown in FIG. 31. The bell type disposable uses capillary action to wick the sample up the tube until it reaches the bulb or vacuum created by depressing the bulb. The sample is dispensed by collapsing the bulb. Anyone skilled in the art would be able to readily reconfigure the design presented herein to be a single use device.

Figure 7:
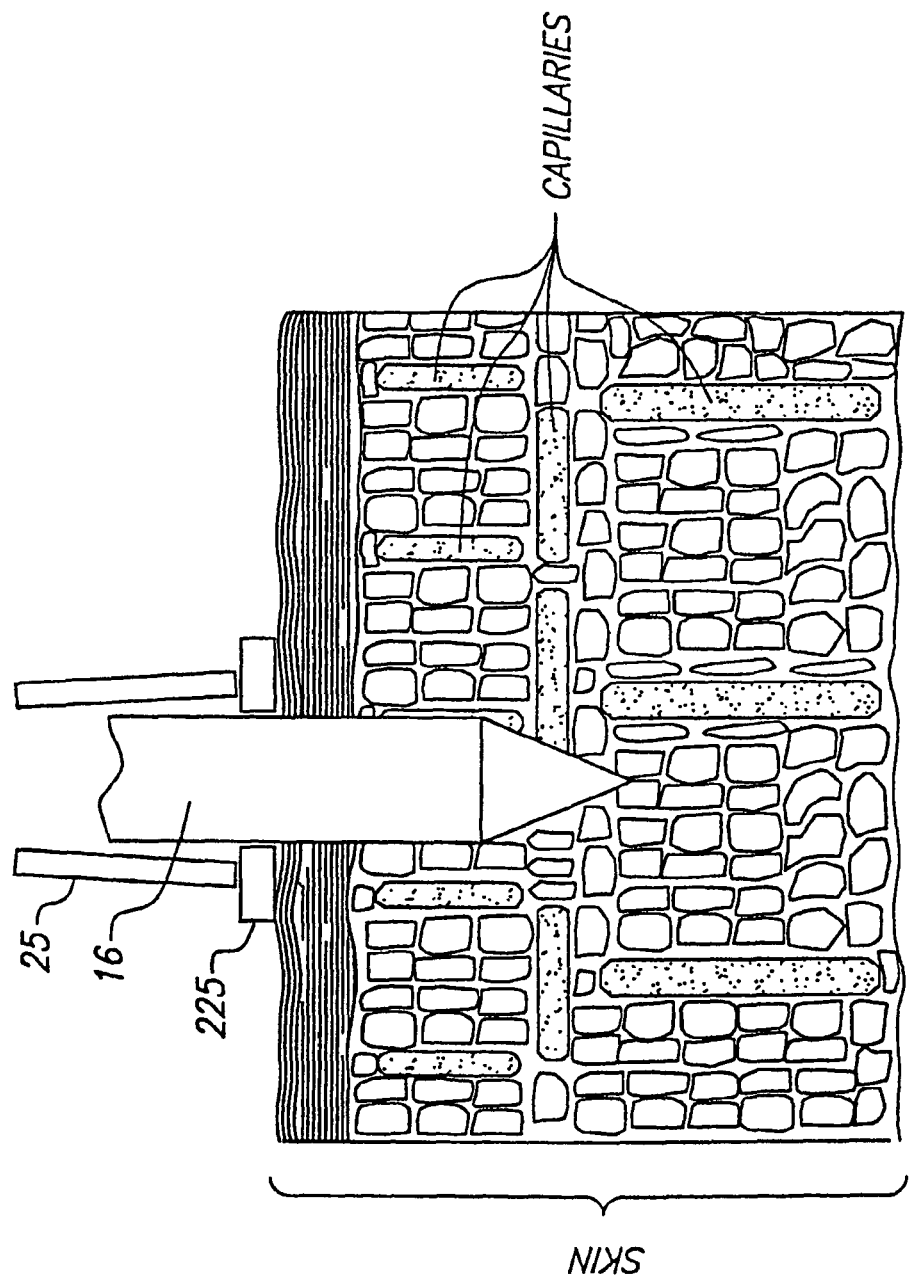
FIG. 7 shows a needle with a collar or sleeve to provide mechanical spreading of the wound during sample collection.

FIG. 7 illustrates the use of a needle 16 with a flexible collar 225 and stimulator ring 25 to hold the wound open during the extraction of the body fluid sample. The collar 225 is affixed to the needle and acts as a stop and as a means of spreading the wound. This provides a means of forcing the wound open during sampling. The collar 225 can be fashioned in various configurations to achieve the same results by one skilled in the art.

Figure 8A:
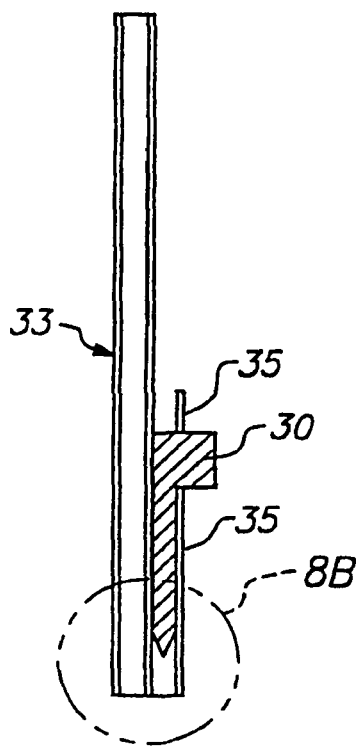
FIGS. 8A and 8B are longitudinal cross section views of a device with a multi-chambered capillary members accommodating a lancet or needle in one chamber and providing another chamber or conduit for sample collection.
Figure 8B:
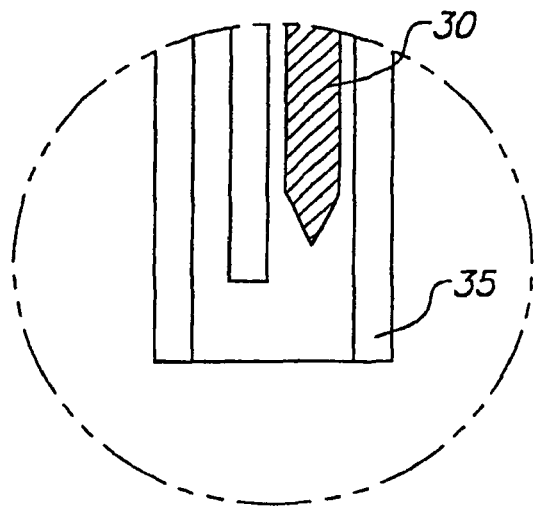
Figure 8C:
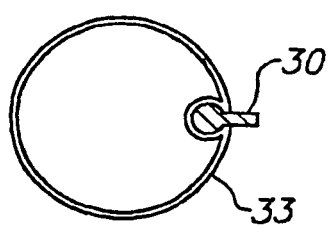
FIGS. 8C, 8D and 8E are top view cross section views of two and three chamber capillary members.
Figure 8D:
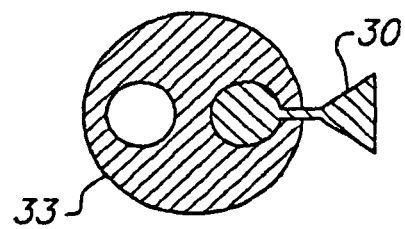
Figure 8E:
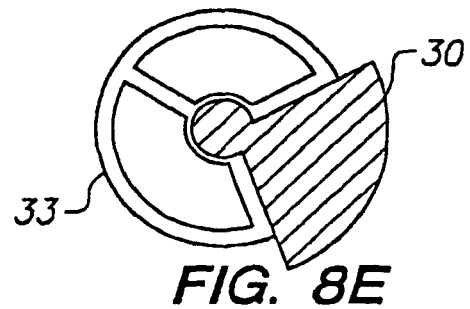

FIG. 8A shows the lancing member is part of a multi-chambered capillary disposable. FIG. 8B provides an exploded view of the end of the device showing the relation ship of lancet 30, disposable 33 and lancet guide tube 35. The multi-chambered capillary disposable can be made from any suitable material. FIGS. 8C, 8D and 8E show various alternatives of this embodiment. One skilled in the art could readily reconfigure a disposable which would be equal to this invention.

The lancet 30 creates the wound and is guided by guide tube 35. The sample is drawn up the sample collection tube/disposable 33. The complete device can either be fashioned as one single disposable or multiple components.

Figure 9A:
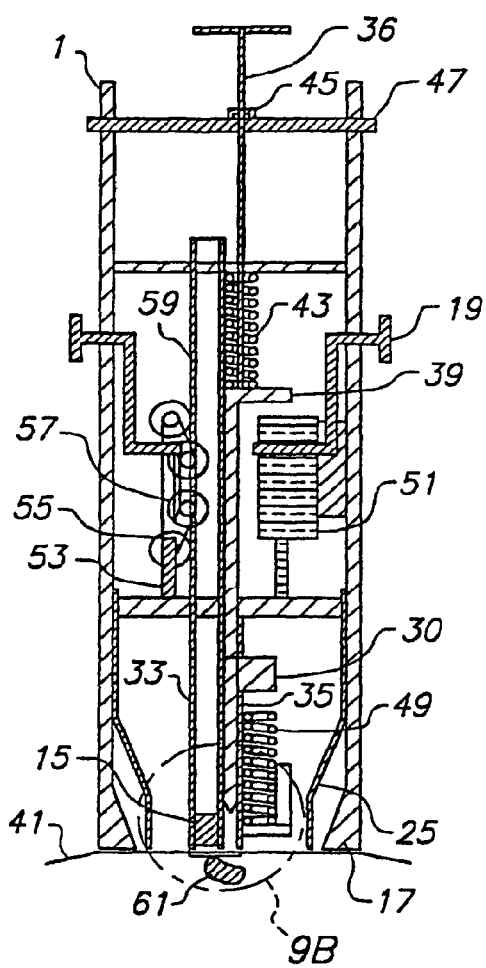
FIGS. 9A and 9B illustrate a longitudinal cross section of a device having a multi-chambered capillary disposable and peristaltic pump to collect a sample.
Figure 9B:
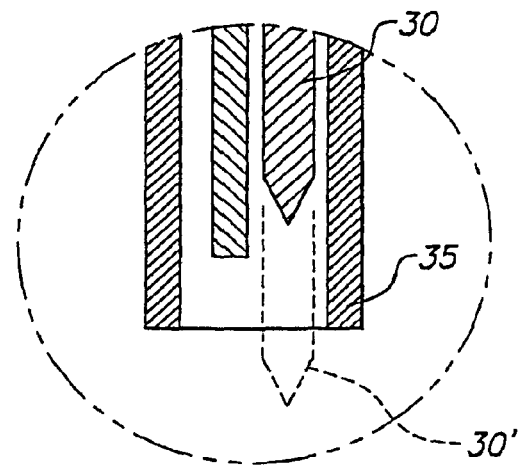

FIG. 9A illustrates a minimally invasive sampling device according to the invention using the alternate capillary disposable blood collection device FIG. 8A which is disposable 33. The device is comprised of numerous components which will be more fully described below. The main body 1 supports the various mechanical components housed within the device. FIG. 9B shows the cutout to allow communication of blood to the sample collection tube.

The main body 1 comprises of an elongated hollow cylindrical tube with openings at both ends. The capillary sampling disposable with lancing member 30, which is part of disposable 33 and is capable of being retracted or deployed so that it can protrude beyond the end of the main body 1, is positioned at one end. The arming plunger assembly 36 protrudes from the other end. The lancing member 30 is guarded by being withdrawn into the needle guide tube 35 which is part of the disposable 33. The needle guide tube 35 acts as the lancing guide and lancet guard. The disposable 33 is attached to the main body 1 so that it is positioned at the appropriate location to guide the lancet and suction up the blood. The striker 39 is projected so as to drive the lancet into the patient 41 by the spring 43 and the arming plunger assembly 36. The arming plunger is locked in place by a cam 45 and trigger 47. A double stop return spring 49 is located and sized to return the lancet 30 back into the disposable 33 needle guide tube 35. The needle guard 17 supports the main body 1 on patient 41.

The double stop return springs 49 provide a mechanism after activation to pull the needle back out of the wound to permit blood 61 accumulation. When the skin is pierced the secondary springs 49 retract the needle from the wound and initiate the stimulation ring 25 oscillation system to force blood flow to the wound. The stimulator ring can oscillate in the preferred range of 1 to 5 mm. The frequency can vary from 5 to 1000 cycles per minute in the preferred embodiment. The oscillation of the stimulator ring 25 is driven by the coils 51 which oscillate the stimulator ring 25 to pump the blood 61 from the surrounding capillaries in the skin into the wound. Each down stroke of the stimulator ring 25 provides this pumping action. This pumping action can be modified to include sinusoidal motion, wobbling, kneading or peristaltic motion which will enhance the blood flood to the wound.

A linkage 53 drives a peristaltic roller system 55 and rollers 57 against the suction tube 59 causing blood 61 to be drawn up the suction tube 59 creating the sample 15.

The stop and adjustment tabs 19 control the depth of penetration of the lancet 30 so that the optimal depth of penetration is reached for a particular sample site.

In another aspect of this invention, electric potential can be applied across the skin to also stimulate blood flow to the wound. This can be accomplished by having separate electrodes present in the device to contact the skin and deliver the electric current at locations desired. Or, the current can be delivered to the skin through components of the device, appropriately insulated internally of course, such as the stimulator ring 25 and sample tube 59, or any other appropriate combination. In general, low voltage DC or AC current can aid in blood flow. The voltage, amperage and cycles (in the case of AC) can be determined by one skilled in the art, but DC voltage in the range, of 1 millivolt to 12 volts will be useful. Likewise, the duration of the applied current or the pulsing thereof can be selected as desired. In a particular example tube 33 in FIG. 9A or needle 16 in FIG. 3 can be the negative electrode and ring 25 in FIG. 9A and FIG. 3 or guard 17 can be the positive electrode.

Figure 9C:
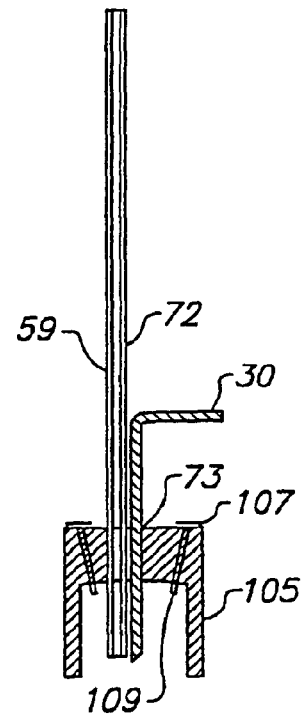
FIG. 9C illustrates in cross section an alternate suction/standoff/lance disposable tip containing contacts for electrically sensing the presence and/or volume of body fluid.

FIG. 9C illustrates a alternate suction/stand off chamber blood collection device 72 which comprises of lance 30, suction tube 59, secondary tube which guides the lance 30, suction/standoff chamber 105, and contacts 107 and 109. The suction tube 59 is mounted in suction/standoff chamber 105 so as to permit the suction tube to be located off the wound to promote bleeding while the wound is stimulated. The contacts provide a means of determining if the sample size is adequate. Contacts 109 are made when adequate volume of blood is present in the cap 105 and these are in communication with contacts 107 which are in communication with the electronic package of the sampler. Once contacts 109 are made by the blood then the circuit is completed signaling the system to stop.

Figure 10:
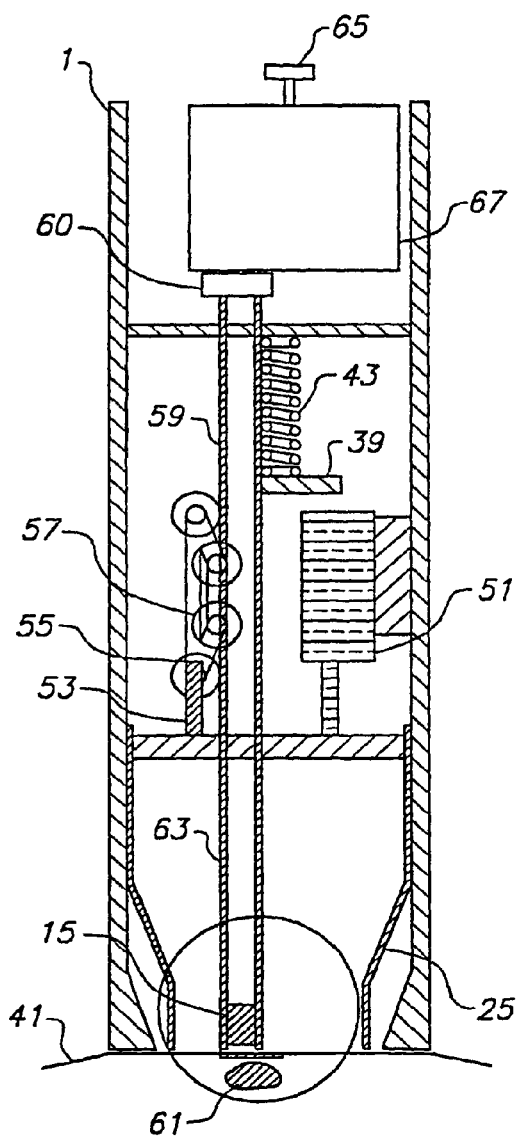
FIG. 10 illustrates in cross section a device with a laser positioned to radiate through the interior of the needle or capillary for piercing the skin.

FIG. 10 illustrates a minimally invasive sampling device according to the invention using the alternate capillary disposable blood collection device and laser 67 lancing mechanism. The device is comprised of numerous components which will be more fully described below. The main body 1 supports the various mechanical components housed within the device.

The main body 1 is comprised of an elongated hollow cylindrical tube with openings at both ends. The capillary sampling disposable with diffusing lens member 60 which is part of disposable 63 is installed in one end of the main body 1. The firing switch 65 protrudes from the other end. The capillary tube 59 acts as the laser guide and sample collection device. The disposable 33 is attached to the main body 1 so that it is positioned at the appropriate location to direct the laser and to suction up the blood. The laser 67 is diffused by going through the lens and creates the wound in the patient.

When the skin is pierced, the laser shuts down. This initiates the stimulation ring 25 oscillation system to force blood flow to the wound. The oscillation of the stimulator ring 25 is driven by the coils 51 which oscillate the stimulator ring 25 so as to pump the blood 61 from the surrounding capillaries in the skin into the wound. Each down stroke of the stimulator ring 25 provides this pumping action. A linkage 53 drives a peristaltic roller system 55 and rollers 57 against the suction tube 59 causing blood 61 to be drawn up the suction tube 59 creating the sample 15. The oscillation of the stimulator ring can have a range of 0 to 8 mm and preferably 1 to 5 mm. The frequency can also vary from 2 to 100 cycles per minute.

In an alternative embodiment for the device of FIG. 10, the lancing means can be a liquid under high pressure or a compressed gas pulse instead of the laser. A pulse of compressed gas, or multiple pulses, can be directed at the skin. In addition, the liquid under pressure or compressed gas pulses can be applied in the annular space between ring 25 and housing 1 to massage and stimulate the skin to increase blood flow to the wound.

It is to be understood that the vacuum employed in the various embodiments of this invention can be used with the capillary tubes, such as 59 in FIG. 10, as well as the needles of FIGS. 4B, 5A and B, and 6A and B.

Figure 11:
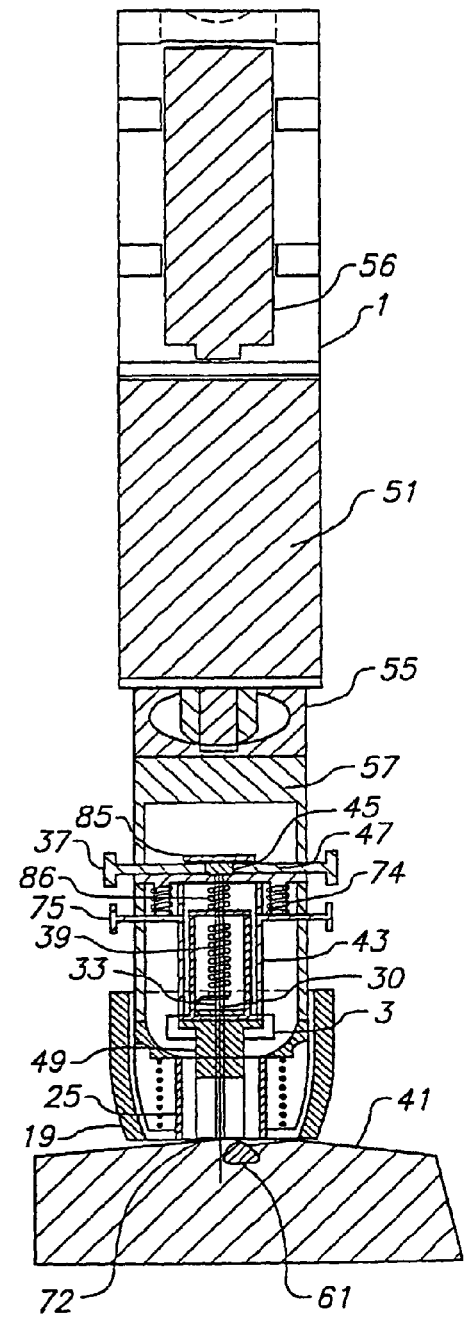
FIG. 11 illustrates in longitudinal cross section in cross section a device of this invention for use with a combined suction/standoff chamber as part of a disposable sample collection system.

FIG. 11 illustrates a minimally invasive sampling device according to the invention using the alternate suction/stand off chamber blood collection device 72 which is more fully described in illustration 9C. The device is comprised of numerous components which will be more fully described below. The main body is 1 which supports the various mechanical components housed within the device.

The main body 1 comprises of an elongated hollow cylindrical tube with openings at both ends. The suction/stand off chamber sampling disposable with lancing member 30 which is part of disposable 72 and is capable of being retracted or deployed so that it can protrude beyond the end of the main body 1 positioned at one end. The arming tabs/trigger 37 protrude from the sides of main body 1. The disposable 72 is attached to the main body 1 so that it is positioned at the appropriate location to guide the lancet and suction up the blood. The striker 39 is projected so as to drive the lancet into the patient 41 by the spring 43 and the arming plunger assembly 37. The arming plunger is locked in place by a cam 45 and trigger 37. A double stop return spring 49 is located and sized to return the lancet 30.

Figure 20A:
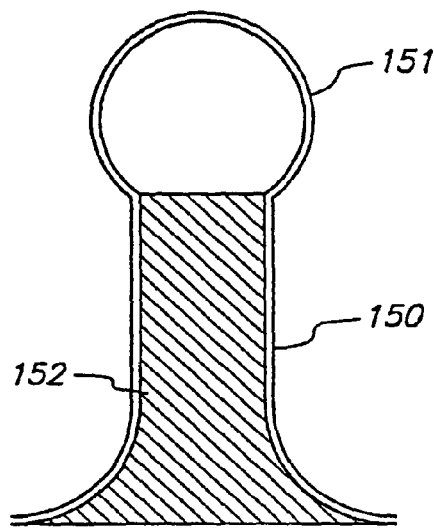
FIGS. 20A, 20B and 20C illustrate a bell shape capillary tube
Figure 20B:
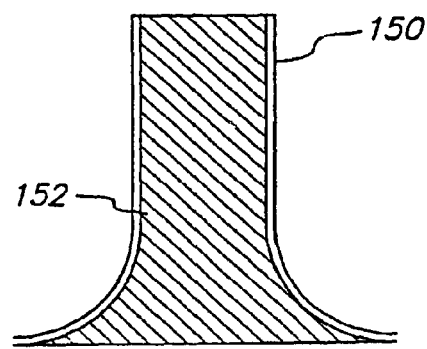
Figure 20C:
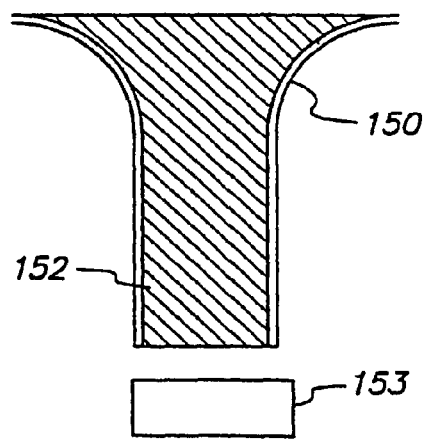

In another aspect, the capillary sample collection tubes used in the various embodiments of this invention, such as 33 in FIGS. 8A and 9A, 59 in FIGS. 9C and 10 and 150 in FIGS. 20A-20C, can be selected to have an affinity for the sample fluid greater than the skin so the fluid or blood will wick into the tube by capillary action. However, the capillary tube is also selected to have less affinity for the sample fluid or blood than a test strip or test device surface of receiving port so that the sample fluid or blood will wick out of the capillary tube into or onto the test strip or device. Such materials for the capillary tube can easily be determined and selected by one skilled in the art, but generally capillary tubes of nylon, PTFE, and the like generally fulfill this function. It will be recognized that the selection of such material for the capillary tube must be made relative to the materials present in and the physical construction the test strip or device, if this aspect of the present invention is to be utilized.

The double stop return springs 49 provide a mechanism after activation to pull the needle back out of the wound to permit blood 61 accumulation. When the skin is pierced, the secondary springs 49 retract the needle from the wound and initiate the stimulation ring 25 oscillation system to force blood flow from the wound. The stimulator ring can oscillate in the preferred range of 1 to 5 mm. The frequency can vary from 5 to 1000 cycles per minute in the preferred embodiment. The oscillation of the stimulator ring 25 is driven by the motor 51 which oscillate the stimulator ring 25 to pump the blood 61 in the surrounding skin capillaries from the wound so the blood can flow to the surface of the skin, bead up, and contact the disposable 72. Each down stroke of the stimulator ring 25 provides this pumping action. The disposable 72 is then lowered onto the blood bead using a secondary motion spring 74 that is released by a secondary motion trigger 75, and suction of the blood initiated. The suction device 85 shown here is a mini syringe which is activated by spring 86 when secondary motion trigger 75 is released causing blood 61 to be drawn up the disposable 72. The stop and adjustment cap 19 controls the depth of penetration of the lancet 30 so that the optimal depth of penetration is reached for a particular sample site.

Figures 12A, 12B:
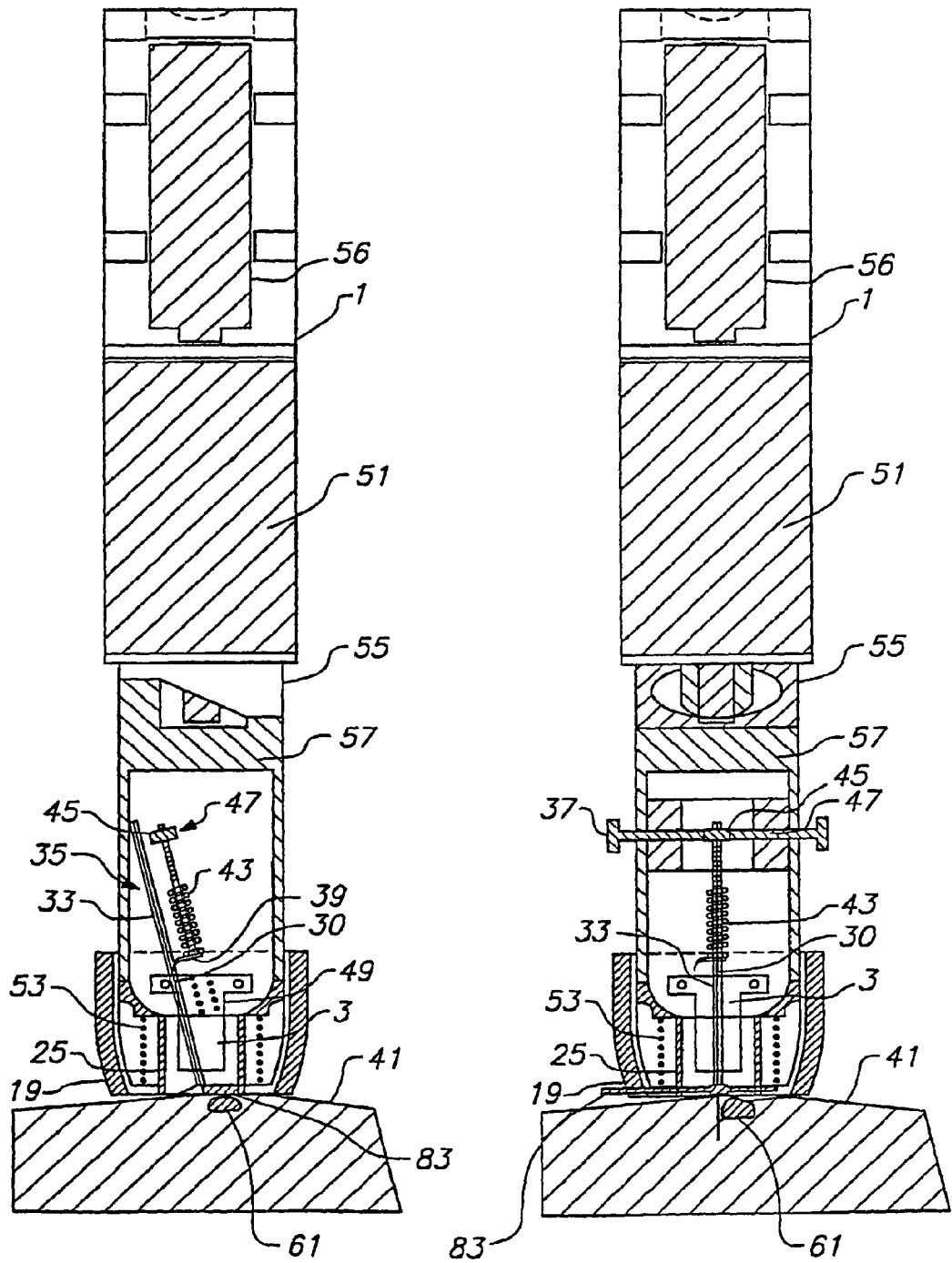
FIGS. 12A and 12B illustrate a longitudinal cross section and side view cross section of a device of this invention having and angled lancet or needle and employing an absorbent strip.

FIGS. 12A and 12B illustrate a minimally invasive sampling device according to the invention using a disposable piercing apparatus, a reusable sampling device and a disposable absorbent test strip 83. FIG. 12A shows the device in a side view and FIG. 12B is a front view. The device is comprised of numerous components which will be more fully described below. The main body is 1 which supports the various mechanical components housed within the device.

The main body 1 comprises of an elongated hollow cylindrical tube with openings at both ends. The lancing member 30 which is part of disposable 33 is capable of being retracted or deployed so that it can protrude beyond the end of the main body 1 is positioned at one end. The arming tabs 37 protrude from the sides of main body 1. The lancing member 30 is guarded by being withdrawn into the tube 35 which is part of the disposable 33. The tube 35 acts as the lancing guide and lancet guard. The disposable 33 is attached to the main body 1 so that it is positioned at the appropriate location to guide the lancet and is held in place by the disposable clamp 3. The striker 39 is projected so as to drive the lancet into the patient 41 by the spring 43 and the arming plunger assembly 36. The arming plunger is locked in place by a cam 45 and trigger 47. A double stop return spring 49 is located and sized to return the lancet 30 back into the tube 35.

The double stop return springs 49 provide a mechanism after activation to pull the needle back out of the wound to permit blood 61 accumulation. When the skin is pierced the secondary springs 49 retract the needle from the wound and initiate the stimulation ring 25 oscillation system to force blood flow to the wound. The cam 55 oscillates the oscillator ring 57 which transmits the motion to stimulation ring 25. The stimulator ring can oscillate in the preferred range of 1 to 5 mm. The frequency can vary from 5 to 1000 cycles per minute in the preferred embodiment. The oscillation of the stimulator ring 25 is driven by the motor 51. The battery 56 provides energy to run the motor 51 which oscillates the stimulator ring 25 to pump the blood 61 from the surrounding capillaries in the skin into the wound. Each down stroke of the stimulator ring 25 compresses the stimulator spring 53 which provides the return motion for the stimulator ring 25. The disposable chemical strip 83 is then lowered onto the blood bead using a secondary motion spring 74 that is released by a secondary motion trigger 75. The blood is absorbed by the disposable chemical strip 83 which fits into a slot in the main body 1 and the stimulator ring 25.

The stop and adjustment tabs 19 control the depth of penetration of the lancet 30 so that the optimal depth of penetration is reached for a particular sample site.

Figure 13:
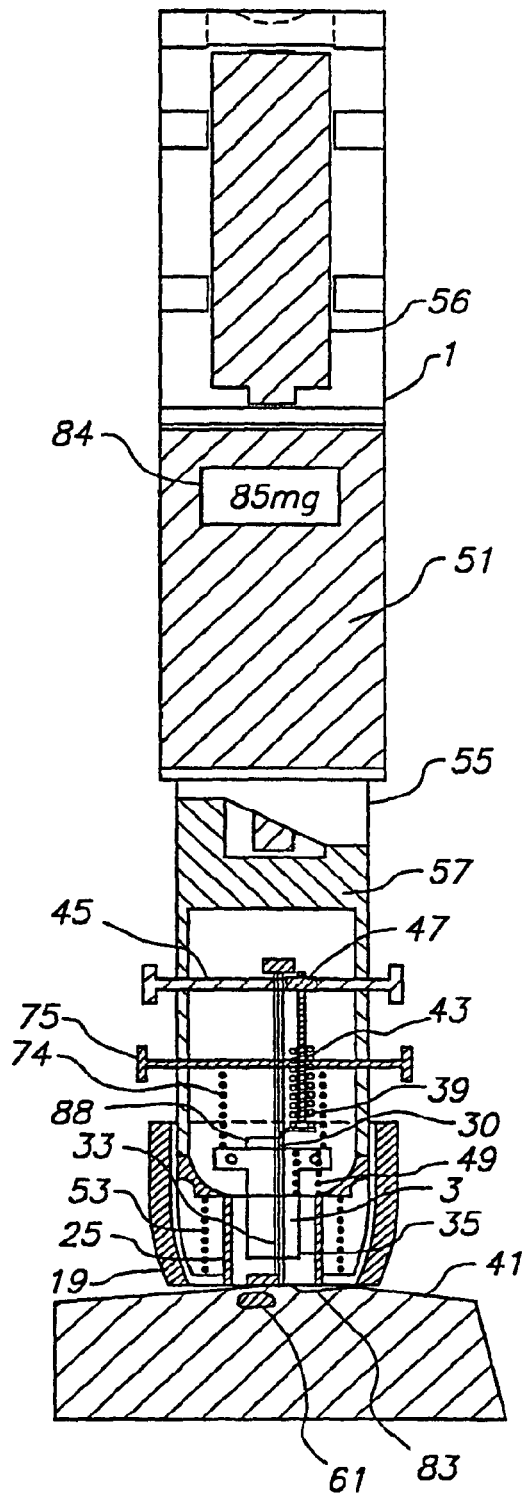
FIGS. 13 and 14 show a longitudinal cross section and a side view cross section of a sampling device of the present invention with an integrated colorimetric instrument test.
Figure 14:
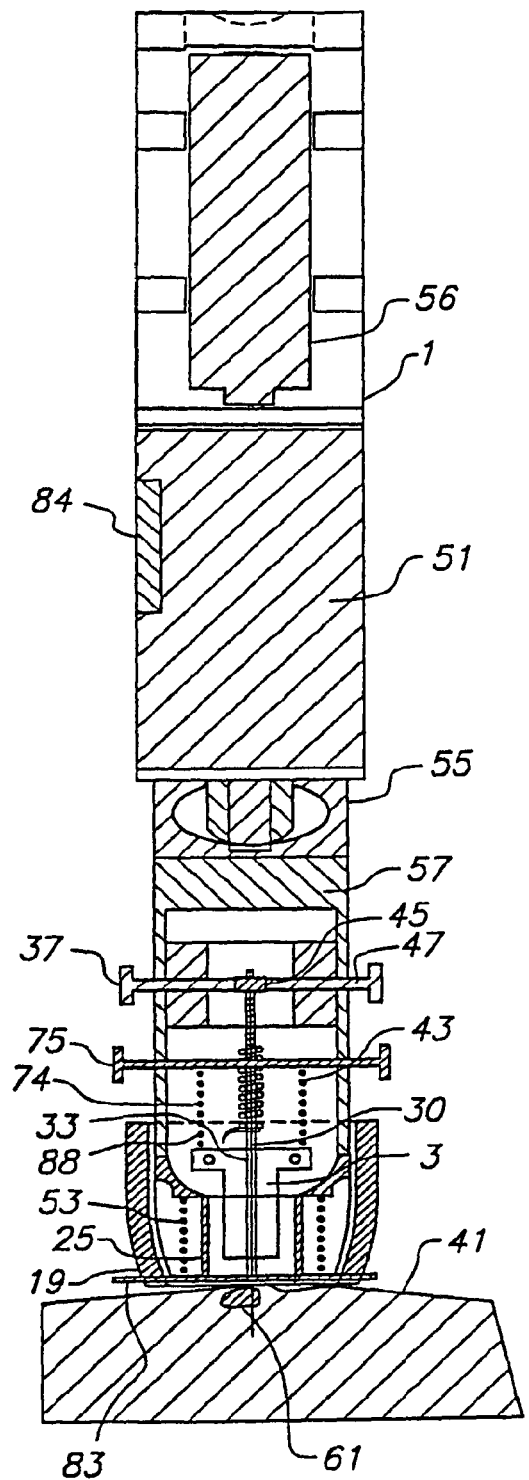

FIGS. 13 and 14 illustrate an integration of the minimally invasive sampling device with a chemical test measurement, such as glucose, and electronic readout according to the invention using a disposable piercing apparatus 33, a reusable sampling device 1, a disposable absorbent test strip 83, and a method of readout such as colorimetric test which is read electronically and has an electronic readout system. FIG. 13 shows the device in a side view and FIG. 14 is a front view. The device is comprised of numerous components which will be more fully described below. The main body is 1 which supports the various mechanical and electrical components housed within the device.

The main body 1 comprises of an elongated hollow cylindrical tube with openings at both ends. The lancing member 30 which is part of disposable 33 is capable of being retracted or deployed so that it can protrude beyond the end of the main body 1 is positioned at one end. The arming tabs 37 protrude from the sides of main body 1. The lancing member 30 is guarded by being withdrawn into the tube 35 which is part of the disposable 33. The tube 35 acts as the lancing guide and lancet guard. The disposable 33 is attached to the main body 1 so that it is positioned at the appropriate location to guide the lancet and is held in place by the disposable clamp 3. The striker 39 is projected so as to drive the lancet into the patient 41 by the spring 43 and the arming plunger assembly 36. The arming plunger is locked in place by a cam 45 and trigger 47. A double stop return spring 49 is located and sized to return the lancet 30 back into the tube 35.

The double stop return springs 49 provide a mechanism after activation to pull the needle back out of the wound to permit blood 61 accumulation. When the skin is pierced the secondary springs 49 retract the needle from the wound and initiate the stimulation ring 25 oscillation system to force blood flow to the wound. The cam 55 oscillates the oscillator ring 57 which transmits the motion to stimulation ring 25. The stimulator ring can oscillate in the preferred range of 1 to 5 mm. The frequency can vary from 5 to 1000 cycles per minute in the preferred embodiment. The oscillation of the stimulator ring 25 is driven by the motor 51. The battery 56 provides energy to run the motor 51 which oscillates the stimulator ring 25 to pump the blood 61 from the surrounding capillaries in the skin into the wound. Each down stroke of the stimulator ring 25 compresses the stimulator spring 53 which provides the return motion for the stimulator ring 25. The disposable chemical strip 83 is then lowered onto the blood bead using a secondary motion spring 74 that is released by a secondary motion trigger 75, and suction of the blood initiated. The blood is absorbed by the disposable chemical strip 83 which has been manufactured into the disposable 33. The strip is then read in place by a LED 88 colorimetric system and analyzed by electronics which are part of the device and displayed on display 84.

The stop and adjustment tabs 19 control the depth of penetration of the lancet 30 so that the optimal depth of penetration is reached for a particular sample site.

Figure 15:
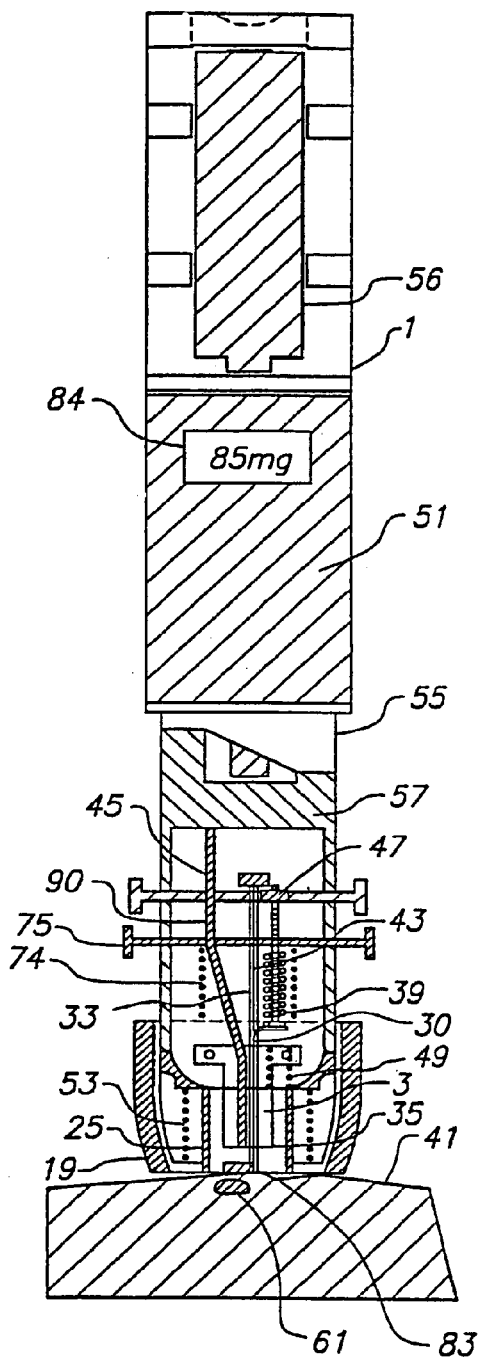
FIG. 15 shows a longitudinal cross section of an sampling device of the present invention With an integrated electrochemical test.

FIG. 15 illustrates an integration of the minimally invasive sampling device with a chemical test measurement, such as glucose, and electronic readout according to the invention using a disposable piercing apparatus 33, a reusable sampling device 1, a disposable absorbent test strip 83, and a method of readout such as a electrochemical test which is read electronically and has an electronic readout system. The device is comprised of numerous components which will be more fully described below. The main body is 1 which supports the various mechanical and electrical components housed within the device.

The main body 1 comprises of an elongated hollow cylindrical tube with openings at both ends. The lancing member 30 which is part of disposable 33 is capable of being retracted or deployed so that it can protrude beyond the end of the main body 1 is positioned at one end. The arming tabs 37 protrude from the sides of main body 1. The lancing member 30 is guarded by being withdrawn into the tube 35 which is part of the disposable 33. The tube 35 acts as the lancing guide and lancet guard. The disposable 33 is attached to the main body 1 so that it is positioned at the appropriate location to guide the lancet and is held in place by the disposable clamp 3. The striker 39 is projected so as to drive the lancet into the patient 41 by the spring 43 and the arming plunger assembly 36. The arming plunger is locked in place by a cam 45 and trigger 47. A double stop return spring 49 is located and sized to return the lancet 30 back into the tube 35.

The double stop return springs 49 provide a mechanism after activation to pull the needle back out of the wound to permit blood 61 accumulation. When the skin is pierced the secondary springs 49 retract the needle from the wound and initiate the stimulation ring 25 oscillation system to force blood flow to the wound. The cam 55 oscillates the oscillator ring 57 which transmits the motion to stimulation ring 25. The stimulator ring can oscillate in the preferred range of 1 to 5 mm. The frequency can vary from 5 to 1000 cycles per minute in the preferred embodiment. The oscillation of the stimulator ring 25 is driven by the motor 51. The battery 56 provides energy to run the motor 51 which oscillates the stimulator ring 25 to pump the blood 61 from the surrounding capillaries in the skin into the wound. Each down stroke of the stimulator ring 25 compresses the stimulator spring 53 which provides the return motion for the stimulator ring 25. The disposable test strip 83 is then lowered onto the blood bead using a secondary motion spring 74 that is released by a secondary motion trigger 75, and suction of the blood initiated. The blood is absorbed by the disposable chemical strip 83 which has been manufactured into the disposable 33. The strip is then read in place by a milliamp/or millivolt sensing electronics depending on the specific chemistry of the test strip. This reading is converted into a chemical concentration by the onboard electronics and displayed on the LCD on the side of the device.

The stop and adjustment tabs 19 control the depth of penetration of the lancet 30 so that the optimal depth of penetration is reached for a particular sample site.

Figure 16:
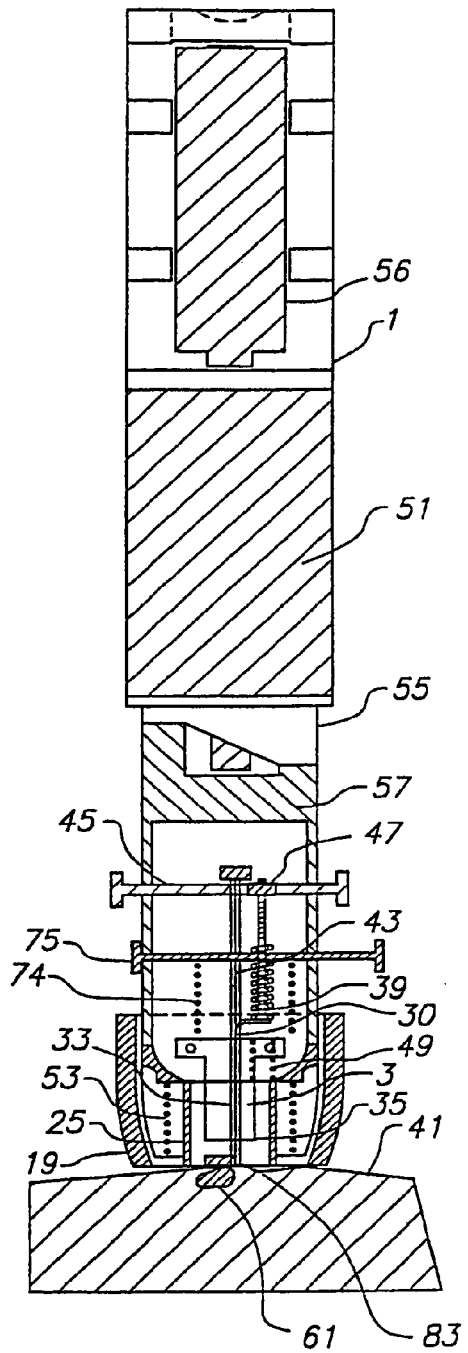
FIGS. 16 and 17 show a longitudinal cross section and a side view cross section of a sampling device of the present invention with an integrated colorimetric visual test.
Figure 17:
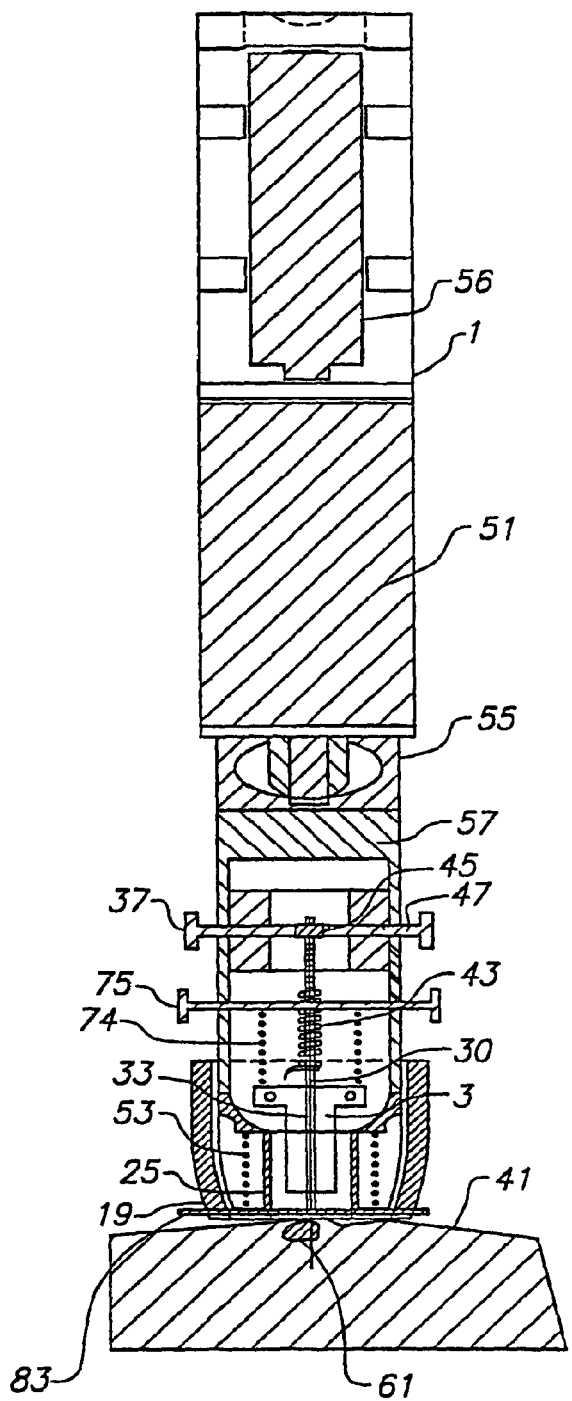

FIGS. 16 and 17 illustrate an integration of the minimally invasive sampling device with a chemical test measurement, such as for glucose, using a disposable piercing apparatus 33, a reusable sampling device 1, a disposable absorbent test strip 83 capable of providing semiquantitative colorimetric results. The device is comprised of numerous components which will be more fully described below. The main body is 1 which supports the various mechanical and electrical components housed within the device.

The main body 1 comprises of an elongated hollow cylindrical tube with openings at both ends. The lancing member 30 which is part of disposable 33 is capable of being retracted or deployed so that it can protrude beyond the end of the main body 1 is positioned at one end. The arming tabs 37 protrude from the sides of main body 1. The lancing member 30 is guarded by being withdrawn into the tube 35 which is part of the disposable 33. The tube 35 acts as the lancing guide and lancet guard. The disposable 33 is attached to the main body 1 so that it is positioned at the appropriate location to guide the lancet and is held in place by the disposable clamp 3. The striker 39 is projected so as to drive the lancet into the patient 41 by the spring 43 and the arming plunger assembly 36. The arming plunger is locked in place by a cam 45 and trigger 47. A double stop return spring 49 is located and sized to return the lancet 30 back into the tube 35.

The double stop return springs 49 provide a mechanism after activation to pull the needle back out of the wound to permit blood 61 accumulation. When the skin is pierced the secondary springs 49 retract the needle from the wound and initiate the stimulation ring 25 oscillation system to force blood flow to the wound. The cam 55 oscillates the oscillator ring 57 which transmits the motion to stimulation ring 25. The stimulator ring can oscillate in the preferred range of 1 to 5 mm. The frequency can vary from 20 to 200 cycles per minute in the preferred embodiment. The oscillation of the stimulator ring 25 is driven by the motor 51. The battery 56 provides energy to run the motor 51 which oscillates the stimulator ring 25 to pump the blood 61 from the surrounding capillaries in the skin into the wound. Each down stroke of the stimulator ring 25 compresses the stimulator spring 53 which provides the return motion for the stimulator ring 25. The disposable chemical strip 83 is then lowered onto the blood bead using a secondary motion spring 74 that is released by a secondary motion trigger 75, and suction of the blood initiated. The blood is absorbed by the disposable chemical strip 83. The strip is then removed and read by the patient.

The stop and adjustment tabs 19 control the depth of penetration of the lancet 30 so that the optimal depth of penetration is reached for a particular sample site.

Figure 18:
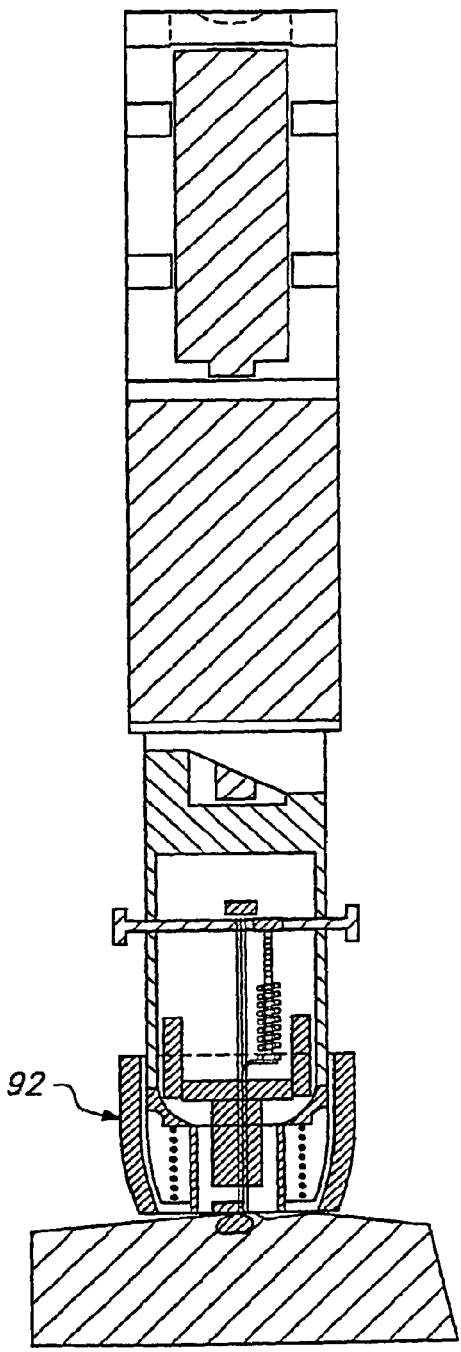
FIG. 18 shows an alternate device which has a completely disposable lower section to minimize blood contamination between uses.

FIG. 18 illustrates an integration of the minimally invasive sampling device using a disposable piercing, stimulating and puncture depth adjustment apparatus 92. The device can assume any of the configurations described by this invention. This modification replaces items 19, 30, 72, 25, 3 on a typical reusable sampling device such as FIG. 11. The disposable unit can incorporate a test strip, a sample container, an electrical sensing unit, or other testing or sampling component.

Figure 19A:
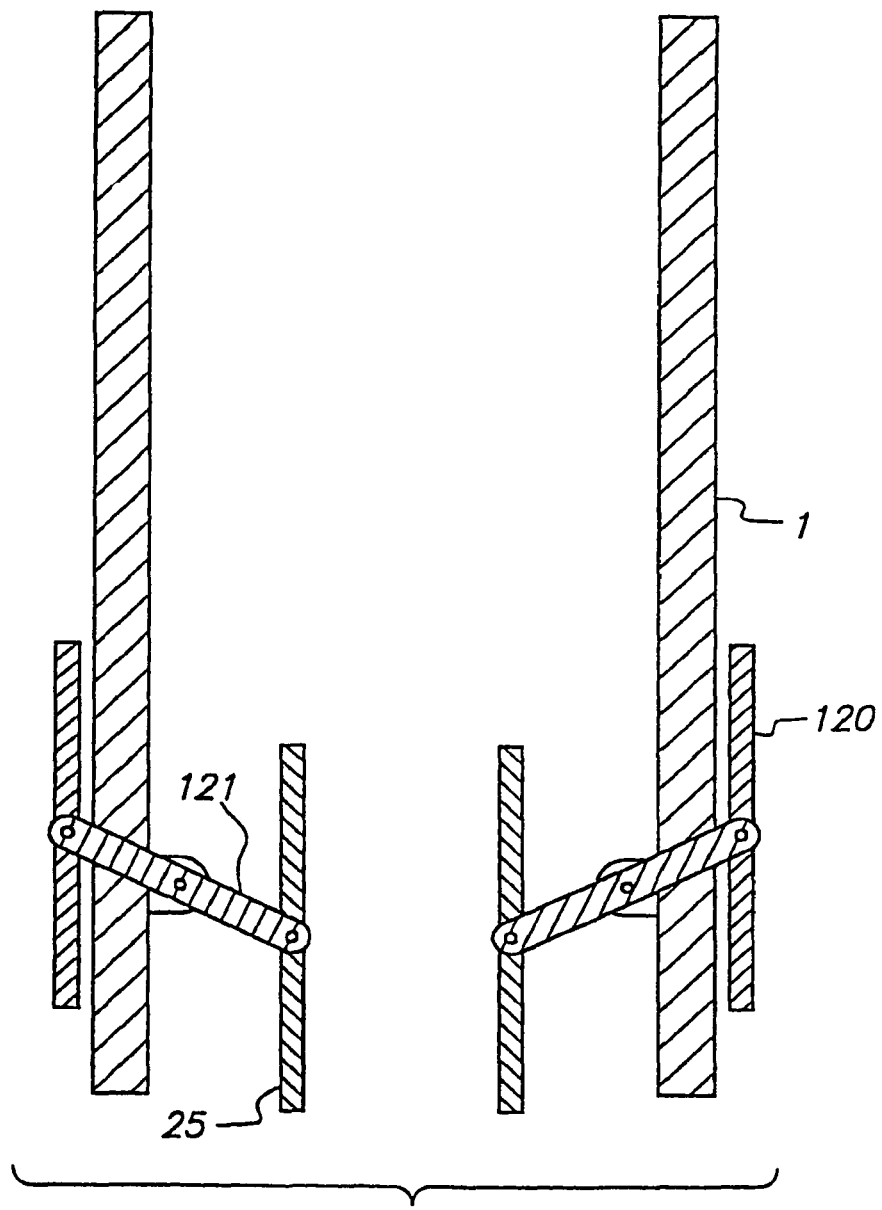
FIG. 19A shows the combination of a dual alternating stimulation ring system.

FIG. 19A shows the concept of a dual alternating stimulation ring system. The secondary stimulation ring 120 alternates it's position 180 degrees out of phase of stimulation ring 25. This creates a peristaltic pumping action on the capillaries adjacent to the wound. This device can be used with any embodiment to increase the blood flow. Link 121 connects the two rings with body 1. The peristaltic pumping results in squeezing the body fluid to the wound by massaging the fluid inward towards the wound.

Figure 19B:
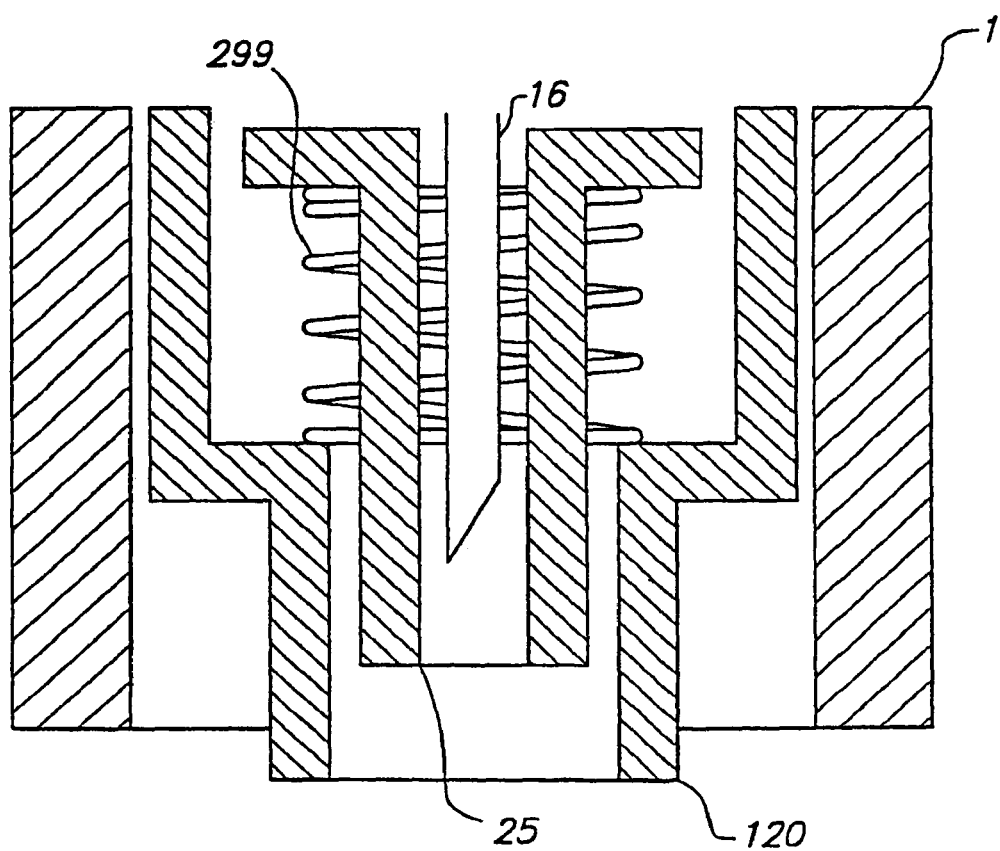
FIG. 19B shows the device with a telescoping stimulator ring.

FIG. 19B shows the concept of concentric collapsing stimulation ring. In this embodiment the inner ring 25 contacts the skin after the outer ring 120. Spring 299 provides resistance and sequencing so that the outer ring 120 contacts the skin prior to inner ring 25. This squeezes the body fluid to the wound by massaging the fluid inward towards the wound.

In an alternate embodiment ring 25 can also function as the sample collection tube after lancing needle 16 is retracted.

In another alternate embodiment compressed gas pulses can be applied in the annular spaces between housing 1 and ring 120 and/or between ring 120 and ring 25 to massage the skin and stimulate blood flow. Such action by compressed gas pulses can be used instead of or in combination with the movement of ring 120 or other stimulation members.

FIG. 20A illustrates a bell shape capillary tube 150 which is used to capture a sample of body fluid. The bell shape capillary is shaped to fit around the drop and it is drawn up the tube until it reaches the bulb 151. This assist in assuring that adequate sample 152 is drawn and the bulb 151 breaks the capillary action. The sample 152 is dispensed by compressing the bulb 151. The capillary can be heated to increase the draw of the capillary tube and the speed of the sample collection.

FIGS. 20B and 20C show an alternative method where the sample 152 is wicked up the tube 150 and the tube is inverted so that the sample can by transferred to a absorbent test pad 153.

Figure 20D:
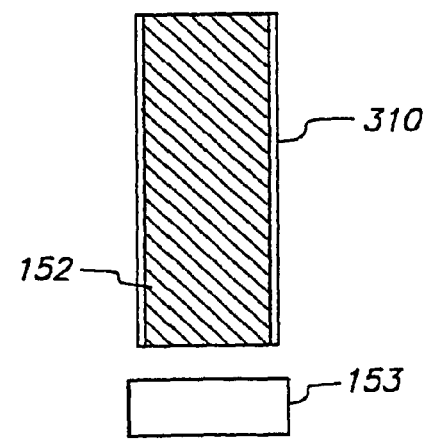
FIG. 20D shows a straight capillary tube with a test strip.

FIG. 20D shows a strait capillary 310 where the sample 152 is wicked up the tube 310 and is transferred to the absorbent test pad 153 by capillary action of the pad.

The tubes shown in 20A, 20B, 20C, and 20D can be modified with a surfactant to increase the ability to wick up the bodily fluid.

Figure 21:
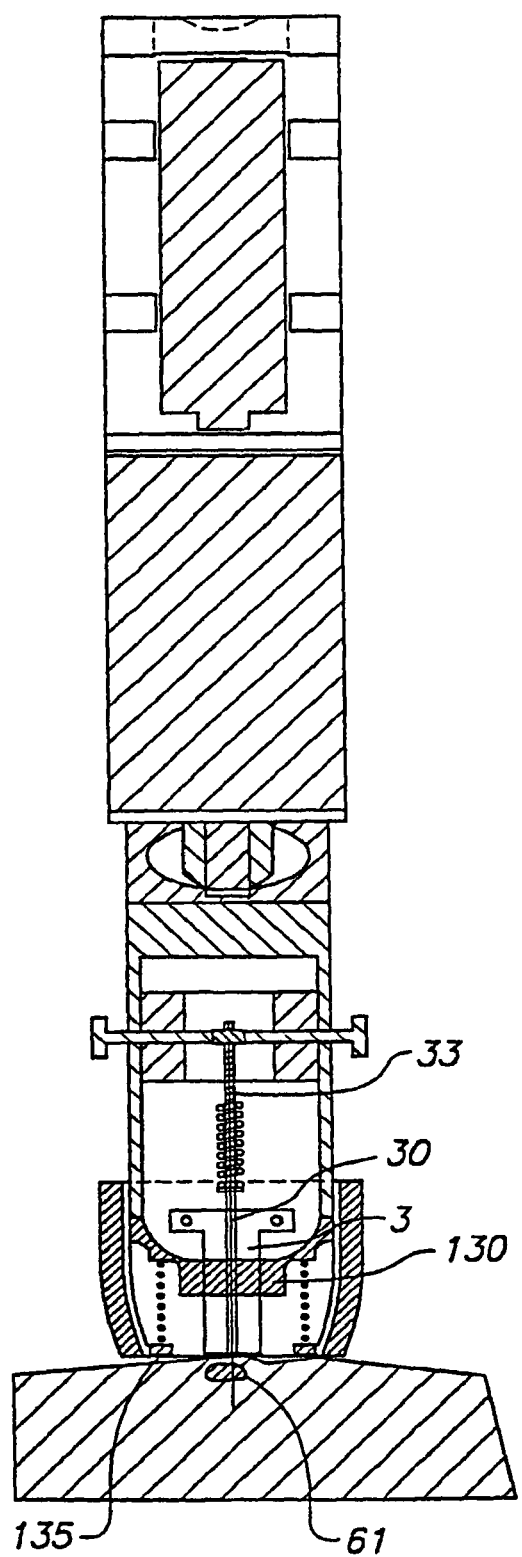
FIG. 21 illustrates a device of this invention with a member to oscillate the needle to stimulate fluid flow from the wound.

FIG. 21 illustrates a device where the oscillation ring 130 is fixtured to disposable clamp 3 to oscillate the needle 33 to stimulate the wound and hold it open so that it does not close around the wound. In addition a heated ring 135 can be used to increase the capillary volume to stimulate blood flow.

Figure 22A:
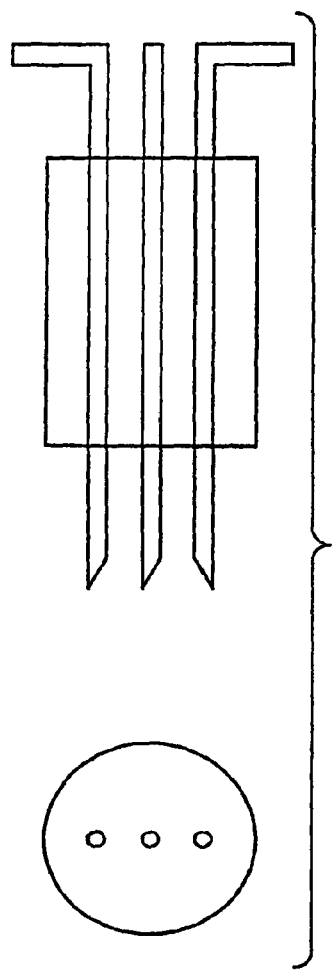
FIG. 22A shows a multiple needle lancing device.

FIG. 22A shows a multiple needle lancing device which is used to cause multiple wounds to increase sample size. The multiple needles are of sufficient size and length to minimize the pain sensation and still generate adequate sample size.

Figure 22B:
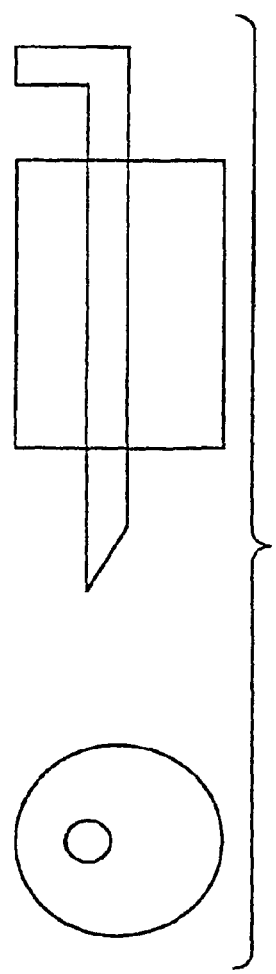
FIG. 22B shows a broader single lancet.

FIG. 22B shows a broader single lancet which is used to cause multiple wounds to increase sample size.

Figure 22C:
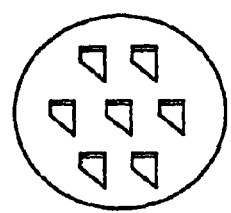
FIGS. 22C and 22D show a die cut sheet which has small multiple barbs formed in the sheet for use as a lance in the present invention.
Figure 22D:
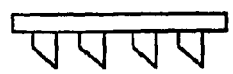

FIGS. 22C and 22D shows a die cut sheet which has small multiple barbs formed in it which is used to cause multiple wounds to increase sample size. The multiple barbs are of sufficient size and length to minimize the pain sensation and still generate adequate sample size.

The lancing device of FIGS. 22A through 22D can be used in the sampling devices disclosed herein.

We claim:

1. A device for sampling body fluid, comprising:
a body portion;
a needle comprising a sharpened distal tip and shaft portion which is slidably disposed within the body portion;
a spring mechanism in the body portion wherein the spring mechanism is configured to move the needle in a first direction relative to the body portion to form an incision in tissue;
a sample container communicating with the needle for receiving the sample from the needle; and
a retraction mechanism configured to retract the needle into the body portion after forming the incision.

2. The device of claim 1 wherein the sharpened distal tip of the needle is covered by the body portion when the needle is in a retracted position and the sharpened distal tip extending beyond a distal end of the body portion when the needle is in an extended position.

3. The device of claim 1, further comprising:
a stop member attached to the body portion configured to limit the depth of penetration of the needle into tissue.

4. A device for sampling body fluid, comprising:
a body portion configured to contain a needle for piercing skin, wherein the needle is slidably disposed within the body portion;
a means for driving the needle to form an incision in skin;
a sample container in fluid communication with the needle for receiving the body fluid sample; and
a means for retracting the needle from the skin.

5. The device of claim 4 wherein a sharpened distal tip of the needle exits a distal end of the body portion at an exit port.

6. The device of claim 4 wherein a sharpened distal tip of the needle is covered by the body portion when the needle is in a retracted position and the sharpened distal tip extending beyond a distal end of the body portion when the needle is in an extended position.

7. The device of claim 4, wherein the means for driving the needle to form the incision in skin includes a spring.

8. The device of claim 4, wherein the means for retracting the needle from the skin includes a spring.

9. The device of claim 4, further comprising:
a stop member configured to limit the depth of penetration of the needle into the skin.

10. A tissue penetrating device, comprising:
a housing;
at least one penetrating member configured to form an incision in tissue, the at least one penetrating member slidably received in the housing;
a penetrating member driver coupled to the at least one penetrating member;
a stop member configured to limit the depth of penetration of the at least one penetrating member into the tissue; and
a retraction mechanism configured to retract the at least one penetrating member after forming the incision.

11. The device of claim 10, further comprising:
wherein the penetrating member driver includes a spring mechanism in the housing that is configured to move the at least one penetrating member in the forward direction.

12. The device of claim 10, wherein the retraction mechanism includes a spring disposed in the housing.

13. The device of claim 10, wherein the at least one penetrating member is a needle.

14. The device of claim 10, further comprising:
a guard positioned over the at least one tissue penetrating member prior to forming the incision with the at least one tissue penetrating member, wherein the guard is attached to an end of the housing.

* * * * *